(12) United States Patent
Yu et al.

(10) Patent No.: US 12,667,689 B2
(45) Date of Patent: Jun. 30, 2026

(54) ASSEMBLY FOR DIVERTING LIQUID FROM A RESPIRATORY DEVICE

(71) Applicant: RESMED PTY LTD, Bella Vista (AU)

(72) Inventors: Tzu-Chin Yu, Sydney (AU); Simon Robert Cork, Sydney (AU); Bing Luo, Sydney (AU); Millen James Rath-May, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 682 days.

(21) Appl. No.: 18/250,683

(22) PCT Filed: Oct. 29, 2021

(86) PCT No.: PCT/AU2021/051270
§ 371 (c)(1),
(2) Date: Apr. 26, 2023

(87) PCT Pub. No.: WO2022/087679
PCT Pub. Date: May 5, 2022

(65) Prior Publication Data
US 2023/0381444 A1    Nov. 30, 2023

(30) Foreign Application Priority Data

Oct. 29, 2020    (AU) ................................ 2020903918

(51) Int. Cl.
*A61M 16/16* (2006.01)
*A61M 16/00* (2006.01)
(52) U.S. Cl.
CPC ........ *A61M 16/16* (2013.01); *A61M 16/0066* (2013.01); *A61M 2205/21* (2013.01)

(58) Field of Classification Search
CPC ...... A61M 16/16–168; A61M 16/0063; A61M 16/0066; A61M 16/0069; A61M 16/0072;
(Continued)

(56) References Cited

U.S. PATENT DOCUMENTS 3,965,894 A    6/1976   Fischer
4,782,832 A    11/1988  Trimble et al.
(Continued)

FOREIGN PATENT DOCUMENTS

WO    WO 98/004310 A1    2/1998
WO    WO 98/034665 A1    8/1998
(Continued)

OTHER PUBLICATIONS

"Respiratory Physiology", by John B. West, Lippincott Williams & Wilkins, 9th edition published 2012 (8 pages).
(Continued)

*Primary Examiner* — Bradley H Philips
(74) *Attorney, Agent, or Firm* — Nixon & Vanderhye P.C.

(57) ABSTRACT

An apparatus is provided to prevent water ingress to a medical device with a housing. Such water ingress may originate, for example, from a connected humidifier. The apparatus consists of an endcap including at least one aperture for selective coupling with a compatible accessory. The end cap is constructed from panels which cooperate to provide an internal fluid passageway for diverting water from the point of ingress to the exterior of the housing.

18 Claims, 22 Drawing Sheets

(58) Field of Classification Search
CPC .. A61M 2205/21; A61M 1/61; A61M 16/109;
A61M 16/0808; A61J 1/1412–1431; F24F
6/12–16
See application file for complete search history.

(56) References Cited

U.S. PATENT DOCUMENTS

| | | | |
|---|---|---|---|
| 4,944,310 A | 7/1990 | Sullivan | |
| 5,653,068 A | 8/1997 | Moody et al. | |
| 5,687,715 A | 11/1997 | Landis | |
| 6,170,207 B1 | 1/2001 | Saindon | |
| 6,532,959 B1 | 3/2003 | Berthon-Jones | |
| 6,581,594 B1 | 6/2003 | Drew et al. | |
| 6,736,353 B1 | 5/2004 | Erben | |
| 7,866,944 B2 | 1/2011 | Kenyon et al. | |
| 8,006,691 B2* | 8/2011 | Kenyon | A61M 16/0057 |
| | | | 122/4 R |
| 8,342,177 B2 | 1/2013 | Porges | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,108,008 B2 | 8/2015 | Stenzler et al. | |
| 9,545,492 B2 | 1/2017 | Dimatteo et al. | |
| 9,546,025 B2 | 1/2017 | Miller et al. | |
| 11,612,712 B2* | 3/2023 | Bertinetti | A61M 16/024 |
| | | | 128/200.24 |
| 2007/0157928 A1 | 7/2007 | Pujol et al. | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2011/0155132 A1* | 6/2011 | Virr | A61M 16/16 |
| | | | 128/203.26 |
| 2017/0072161 A1* | 3/2017 | Iwatschenko | A61M 16/109 |
| 2017/0095635 A1 | 4/2017 | Huby | |
| 2017/0246373 A1 | 8/2017 | Günther et al. | |
| 2017/0348505 A1 | 12/2017 | Doo et al. | |
| 2017/0361053 A1 | 12/2017 | Dimatteo et al. | |
| 2019/0175865 A1 | 6/2019 | Hermez | |

| | | | |
|---|---|---|---|
| 2020/0179629 A1* | 6/2020 | Burgess | A61M 16/026 |
| 2020/0297953 A1 | 9/2020 | Kenyon et al. | |
| 2021/0093825 A1* | 4/2021 | Lin | A61M 16/1095 |

FOREIGN PATENT DOCUMENTS

| | | | | |
|---|---|---|---|---|
| WO | WO 00/38772 A1 | 7/2000 | | |
| WO | WO 00/078381 A1 | 12/2000 | | |
| WO | WO 02/066106 A1 | 8/2002 | | |
| WO | WO 2004/073778 A1 | 9/2004 | | |
| WO | WO 2005/063328 A1 | 7/2005 | | |
| WO | WO 2006/074513 A1 | 7/2006 | | |
| WO | WO 2006/130903 A1 | 12/2006 | | |
| WO | WO 2008/024001 A1 | 2/2008 | | |
| WO | WO 2009/052560 A1 | 4/2009 | | |
| WO | WO 2010/135785 A1 | 12/2010 | | |
| WO | WO 2012/171072 A1 | 12/2012 | | |
| WO | WO 2013/020167 A1 | 2/2013 | | |
| WO | WO 2014/015382 A1 | 1/2014 | | |
| WO | WO 2014/138804 A1 | 9/2014 | | |
| WO | WO-2018126299 A1 * | 7/2018 | A61M 16/1095 |
| WO | WO 2018/177794 A1 | 10/2018 | | |
| WO | WO 2019/119058 A1 | 6/2019 | | |
| WO | WO 2019/183680 A1 | 10/2019 | | |
| WO | WO 2020/064784 A1 | 4/2020 | | |
| WO | WO-2020212902 A1 * | 10/2020 | A61M 16/107 |
| WO | WO-2022247255 A1 * | 12/2022 | A61M 16/16 |

OTHER PUBLICATIONS

International Preliminary Report on Patentability dated Sep. 16, 2022 issued in International Application No. PCT/AU2021/051270 (5 pages).
International Search Report dated Jan. 24, 2022 issued in International Application No. PCT/AU2021/051270 (15 pages).
Written Opinion of the International Searching Authority dated Jan. 24, 2022 issued in International Application No. PCT/AU2021/051270 (6 pages).

* cited by examiner

4500

ASSEMBLY FOR DIVERTING LIQUID FROM A RESPIRATORY DEVICE

CROSS-REFERENCE TO RELATED APPLICATIONS

This application is the U.S. national phase of International Application No. PCT/AU2021/051270 filed Oct. 29, 2021 which designated the U.S. and claims priority to Australian Patent Application No. 2020903918 filed Oct. 29, 2020, the entire contents of each of which are hereby incorporated by reference.

BACKGROUND OF THE TECHNOLOGY

Field of the Technology

The present technology relates to one or more of the screening, diagnosis, monitoring, treatment, prevention and amelioration of respiratory-related disorders. The present technology also relates to medical devices or apparatus, and their use. The present technology further relates to an assembly for preventing the ingress of liquid into a medical device, particularly a respiratory therapy device.

Description of the Related Art

Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *"Respiratory Physiology"*, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |

-continued

| RPT Device name | A-weighted sound pressure level dB(A) | Year (approx.) |
|---|---|---|
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices may include for example, a high flow therapy device configured to provide a high flow therapy. In this regard, some respiratory therapies may aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients. Additionally, patient error or accident can result in liquids spilling from the tub of conventional humidifiers, that liquid subsequently coming into contact with electrical or delicate mechanical components of the RPT device. This can result in injury to the patient and/or malfunction of the device. A need therefore exists to protect the electrical and mechanical components of RPT devices from the ingress of water, particularly when connected to humidifiers.

Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical. Recently, companies that manufacture large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses or "boli", each bolus timed to coincide with the start of inspiration. This therapy mode is known as pulsed or demand (oxygen) delivery (POD), in contrast with traditional continuous flow delivery more suited to stationary oxygen concentrators.

BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

A further aspect of the present technology is to provide a liquid diversion assembly suitable for use between, for example, an RPT device and a humidifier, comprising multiple panels. These panels are constructed such that when they are connected they form one or more internal passageways. These passageways are configured to divert liquid from the humidifier away from the inner components of the RPT device and out through the RPT device housing into the ambient environment. The passageways may be formed around any inlets/outlets, coupling components or electrical connectors in various configurations.

An aspect of one form of the present technology is a liquid diversion assembly for a medical device that includes a housing. The liquid diversion assembly comprises an end cap in association with the housing, the end cap comprising at least one aperture for selective coupling with a compatible accessory, wherein the end cap comprises at least one internal fluid passageway in fluid communication with the at least one aperture to divert liquid to an exterior of the housing.

In examples, the end cap may comprise a plurality of panels, each panel having an interior surface and an exterior surface, wherein the plurality of panels are joined together to form the end cap and define the at least one internal fluid passageway therebetween. In examples the plurality of panels comprises a proximal panel proximal to the medical device in use, comprising a first interior surface and a first exterior surface, and a distal panel distal to the medical device in use, comprising a second interior surface and a second exterior surface. In examples the liquid diversion assembly comprises at least one wall extending between the first interior surface and the second interior surface, wherein the internal fluid passageway is at least in part defined by the at least one wall, the first interior surface, and the second interior surface.

In examples the proximal panel comprises at least one recess in the first interior surface, wherein the at least one aperture is between the second exterior surface and the second interior surface of the distal panel, and wherein the at least one recess is substantially aligned with the at least one aperture. In examples the at least one wall extends along the first interior surface and the second interior surface to substantially surround the at least one recess, wherein the at least one wall comprises a gap in a position inferior to the at least one recess, configured to permit flow of liquid from the internal fluid passageway to the exterior of the end cap. In examples an inferior surface of the at least one recess is angled from a superior position to an inferior position at the first interior surface.

In examples, the proximal panel may comprise a guide protrusion surrounding each one of the at least one recesses, wherein the guide protrusion projects from the first interior surface towards the second interior surface, wherein an air gap is retained between the guide protrusion and the second interior surface. In examples the guide protrusion may comprise a radially outward facing surface and a radially inward facing surface meeting at an apex. In examples each guide protrusion may comprises a raised base surrounding the recess, and a guide protrusion extending from the raised base. In examples a plateau portion may be provided between a radially outward edge of the raised base and the guide protrusion.

In examples, the at least one wall may comprise a first wall extending from the first interior surface, and a second wall extending from the second interior surface, wherein the proximal panel and the distal panel are configured such that when connected the first wall and the second wall cooperate to form the internal fluid passageway.

In examples, the panels may be joined to form a unitary part. In examples, the panels may be joined by mechanical means (for example using fasteners, and/or engineering fit), and/or bonding (for example thermal bonding such as heat staking, or ultrasonic welding).

In examples, the compatible accessory may be a humidifier. In examples, the medical device may be a ventilator.

An aspect of one form of the present technology is an apparatus for supplying a flow of breathable gas at a positive pressure for respiratory therapy, wherein the apparatus comprises: a pressure generator for generating the flow of breathable gas and supplying the flow to an outlet; a housing which contains at least the pressure generator; and a liquid diversion assembly substantially as described herein, wherein the end cap of the liquid diversion assembly is configured to be secured relative to the housing containing at least the pressure generator.

An aspect of one form of the present technology is a respiratory treatment system, comprising an apparatus for supplying a flow of breathable gas at a positive pressure for respiratory therapy substantially as described herein, and a humidifier apparatus to change the absolute humidity of a flow of air for delivery to an entrance of the airways of a patient, the change being compared to the absolute humidity of ambient air, wherein the humidifier apparatus is configured to be selectively coupled to the apparatus for supplying a flow of breathable gas via the at least one aperture of the end cap.

In examples, the apparatus comprises an end cap in association with the housing. In examples the end cap is configured to selectively couple with the chamber and reservoir. In examples the end cap is positioned so that it forms a seal in conjunction with the housing. In examples the end cap forms a physical barrier between the pneumatic block and the optional chamber and reservoir.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

Respiratory Therapy Systems

RPT Device

Figure 1A:
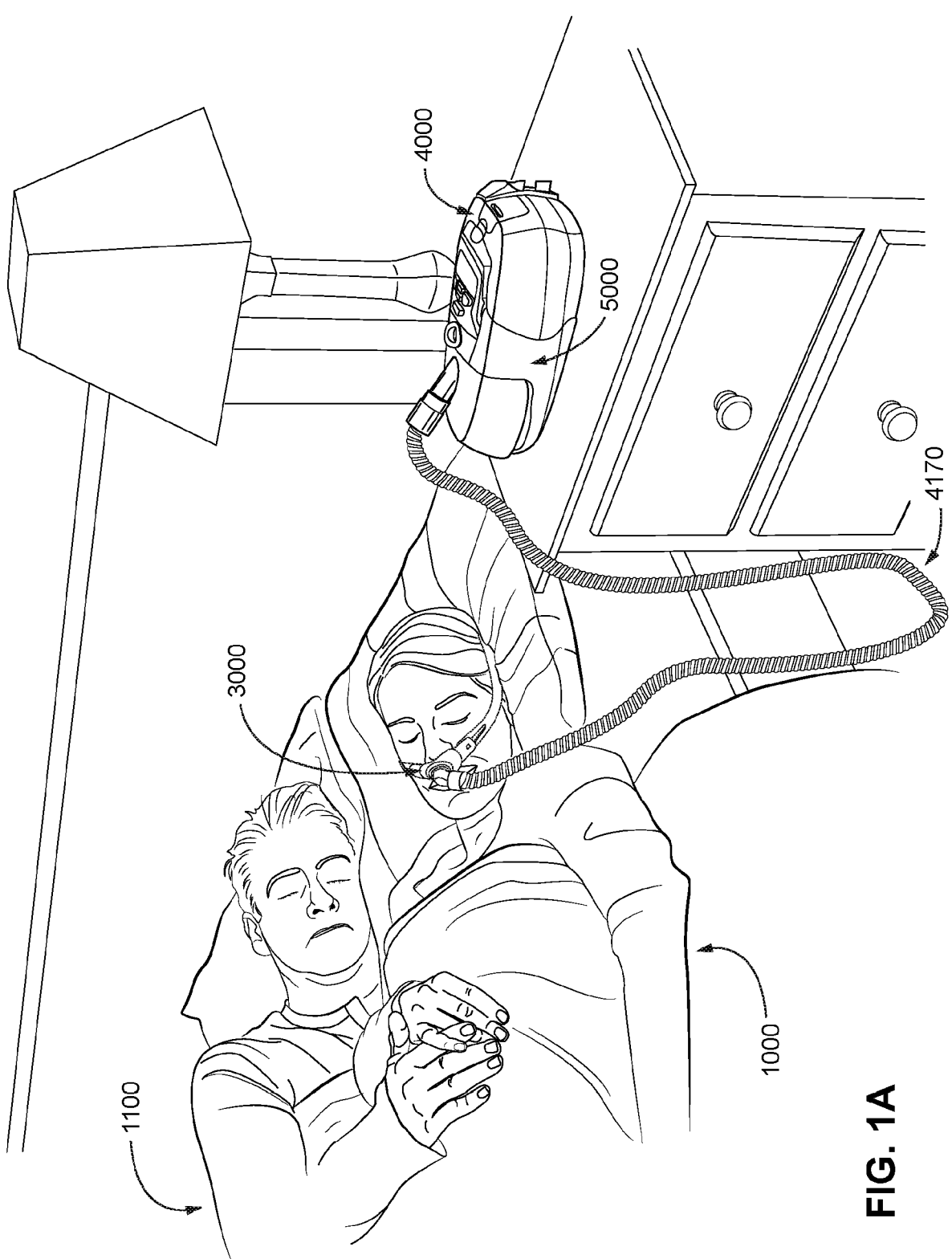
FIG. 1A shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.
Figure 1B:
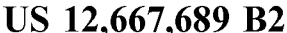
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
Figure 1C:
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.
Figure 2A:
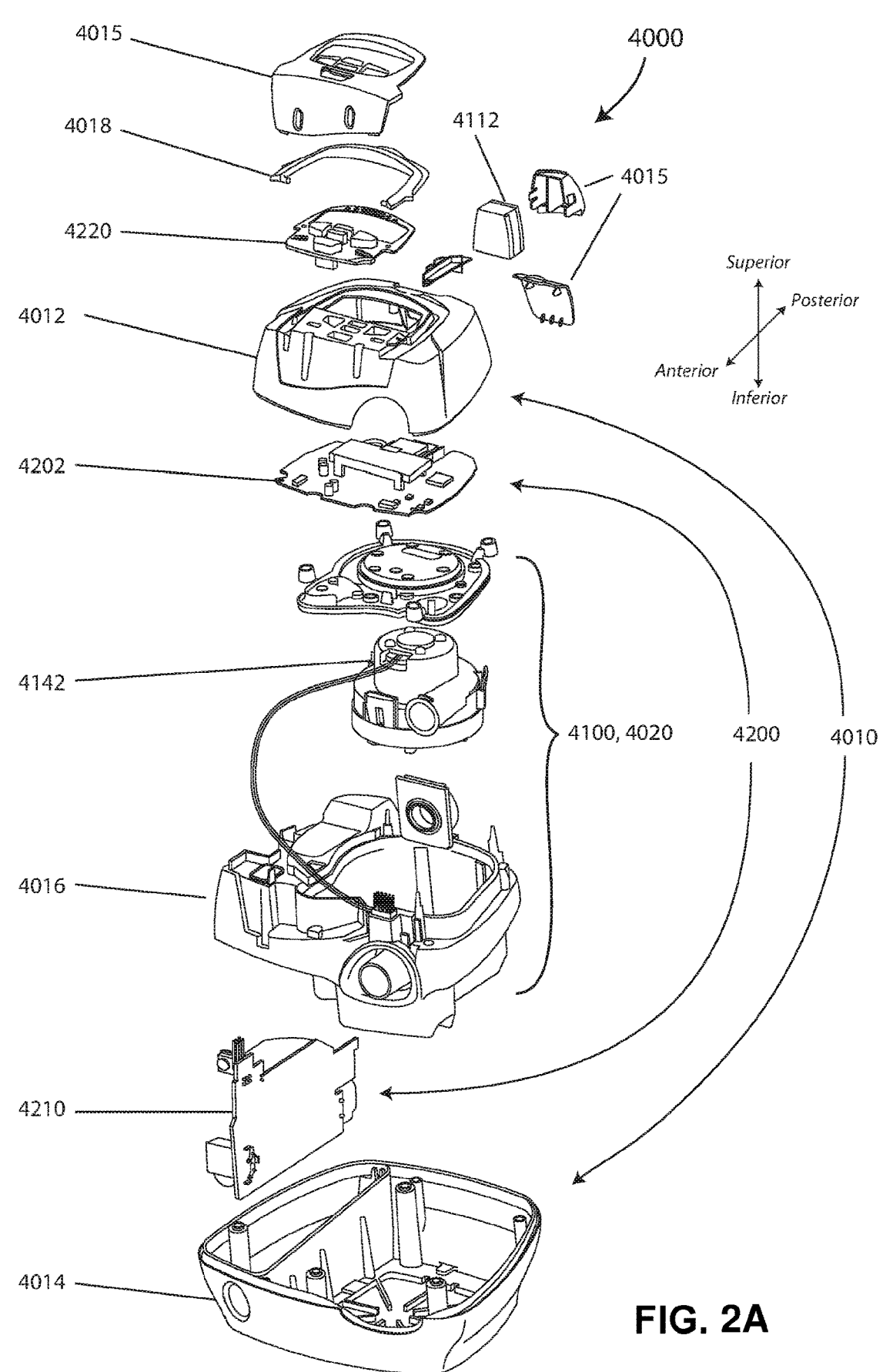

FIG. 2A shows an RPT device in accordance with one form of the present technology.

Figure 2B:
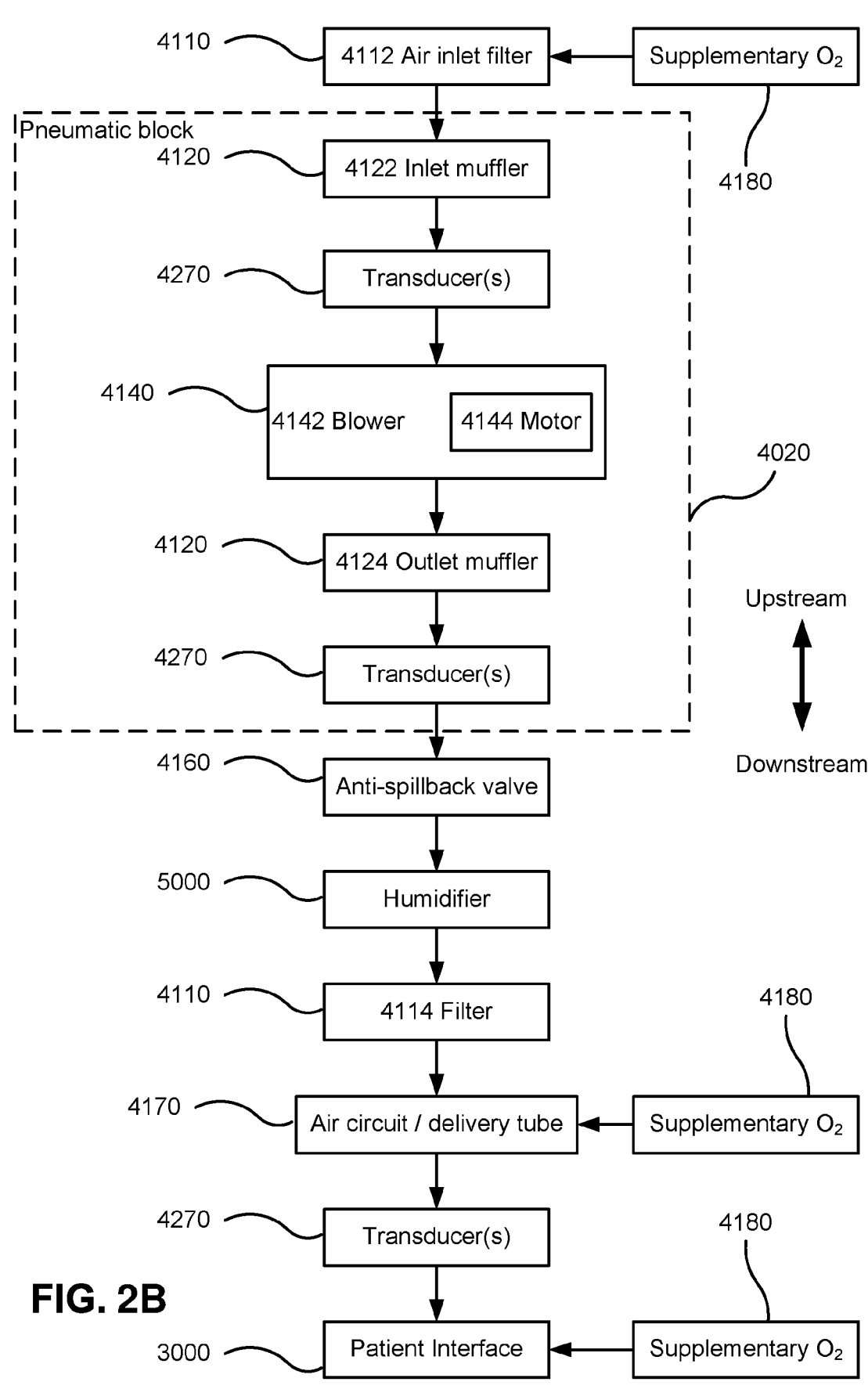

FIG. 2B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 2C:
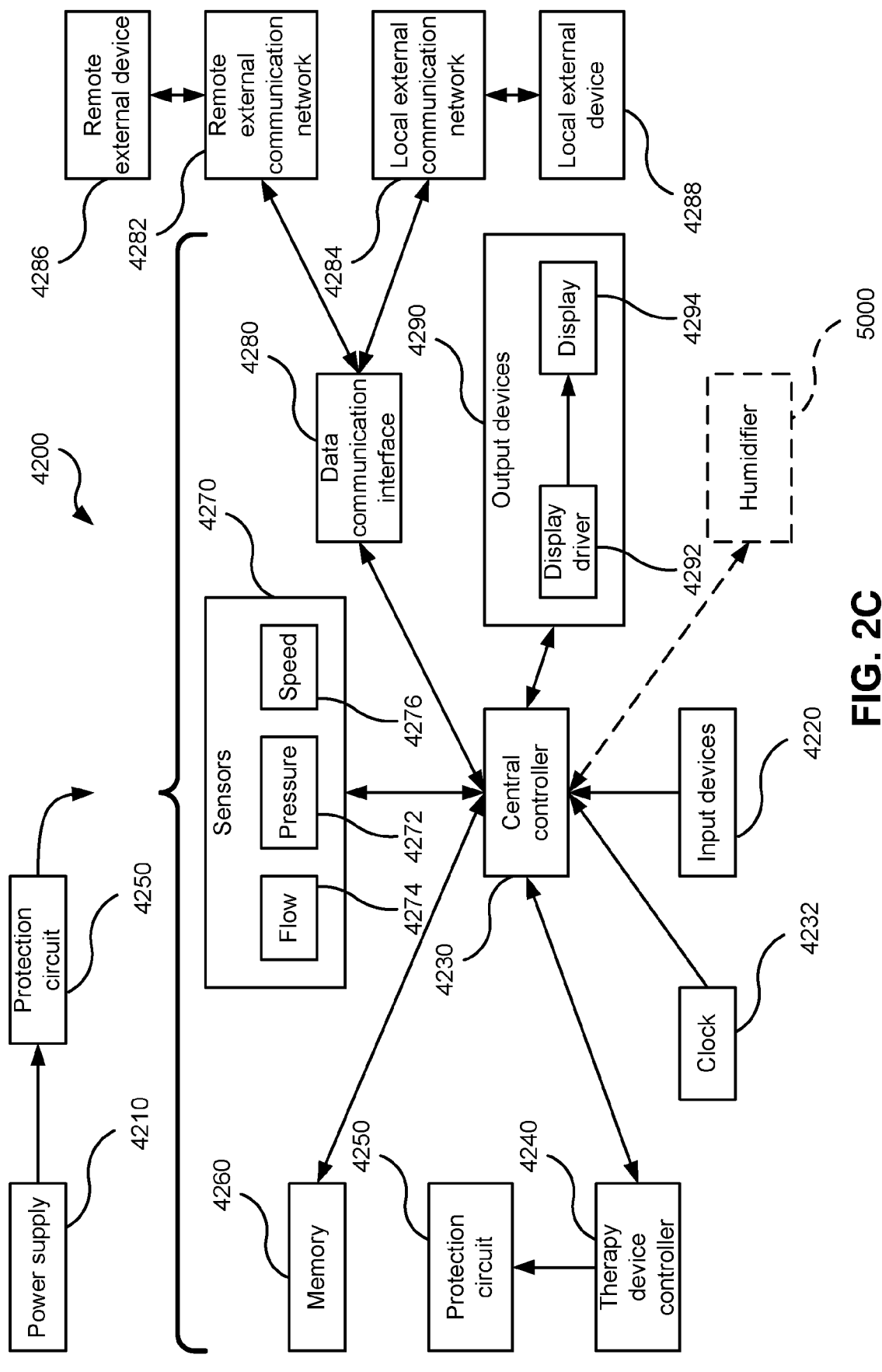

FIG. 2C is a schematic diagram of the electrical components of an RPT device in accordance with one form of the present technology.

Figure 2D:
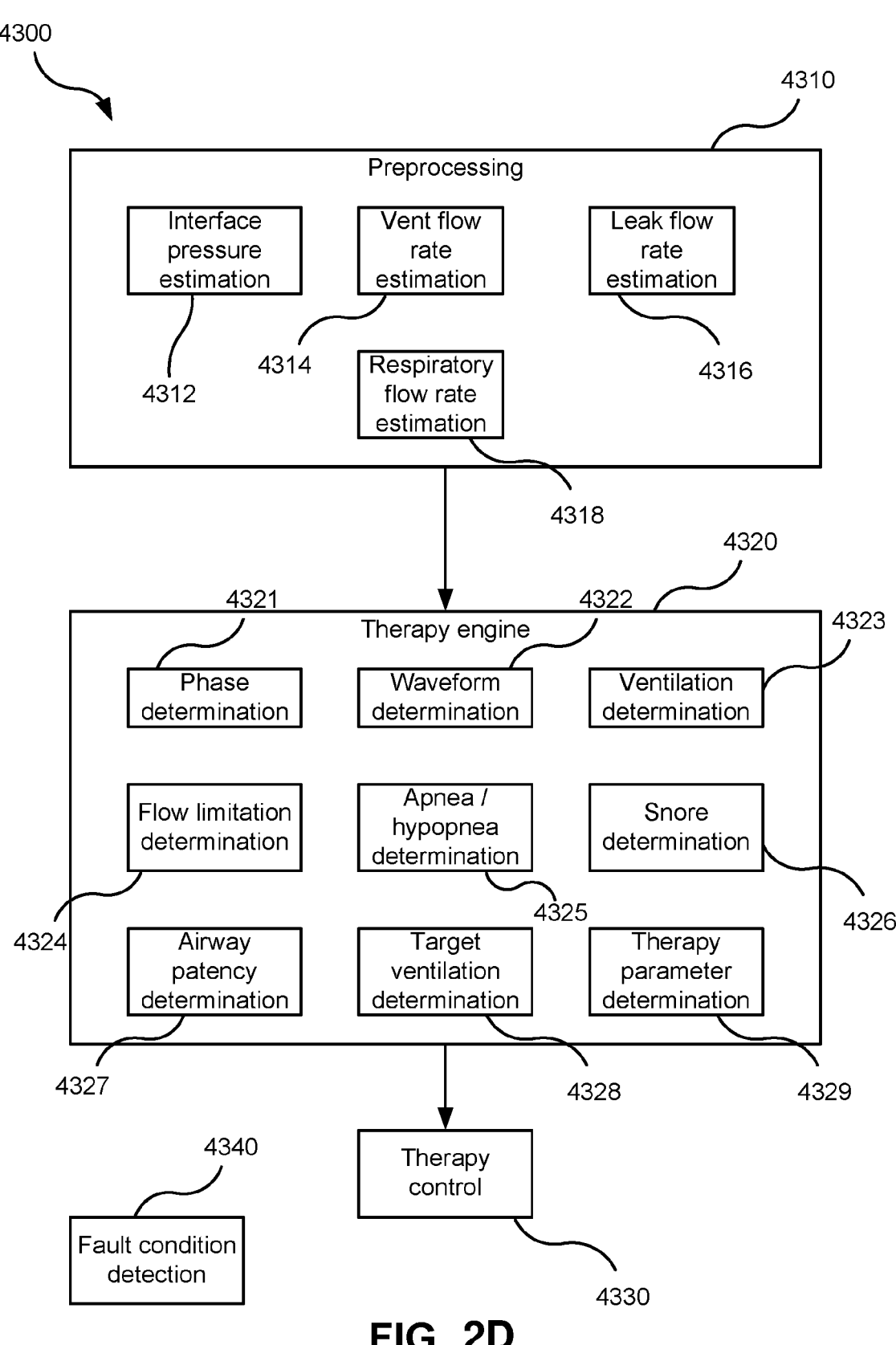

FIG. 2D is a schematic diagram of the algorithms implemented in an RPT device in accordance with one form of the present technology.

Figure 2E:
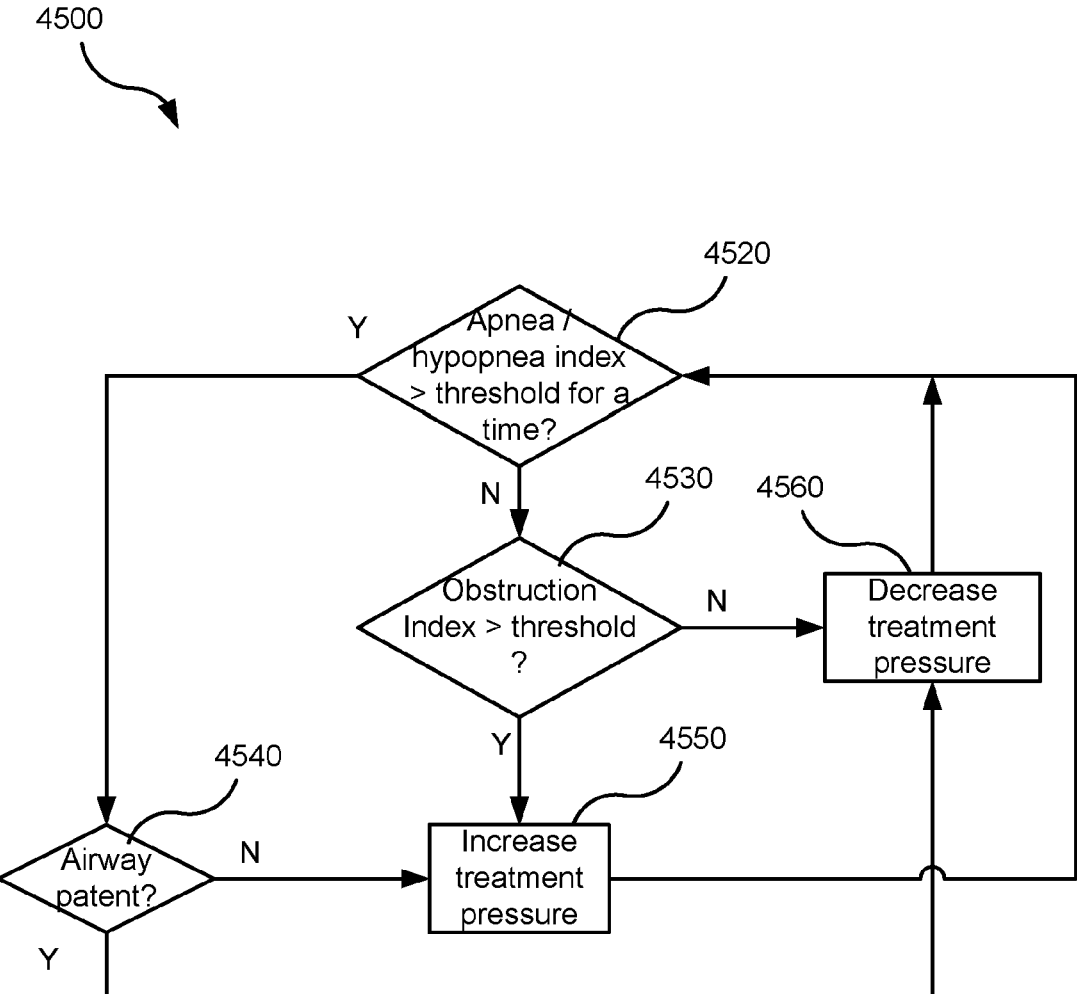

FIG. 2E is a flow chart illustrating a method carried out by the therapy engine module of FIG. 2D in accordance with one form of the present technology.

Humidifier

Figure 3A:
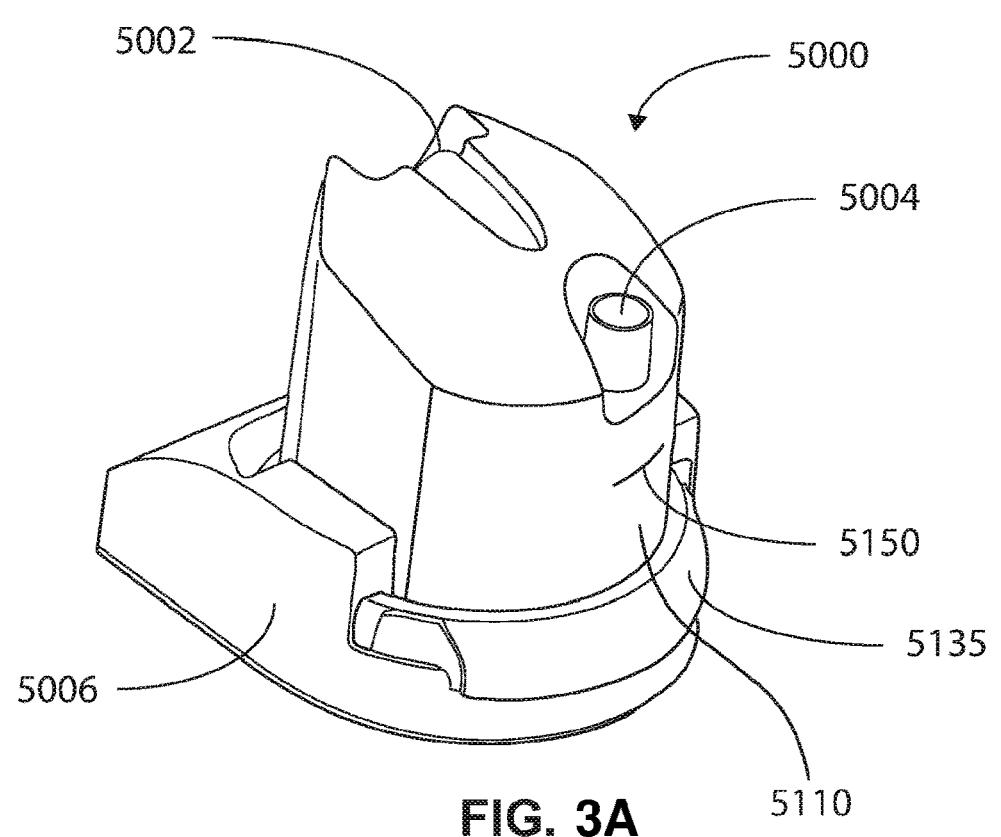

FIG. 3A shows an isometric view of a humidifier in accordance with one form of the present technology.

Figure 3B:
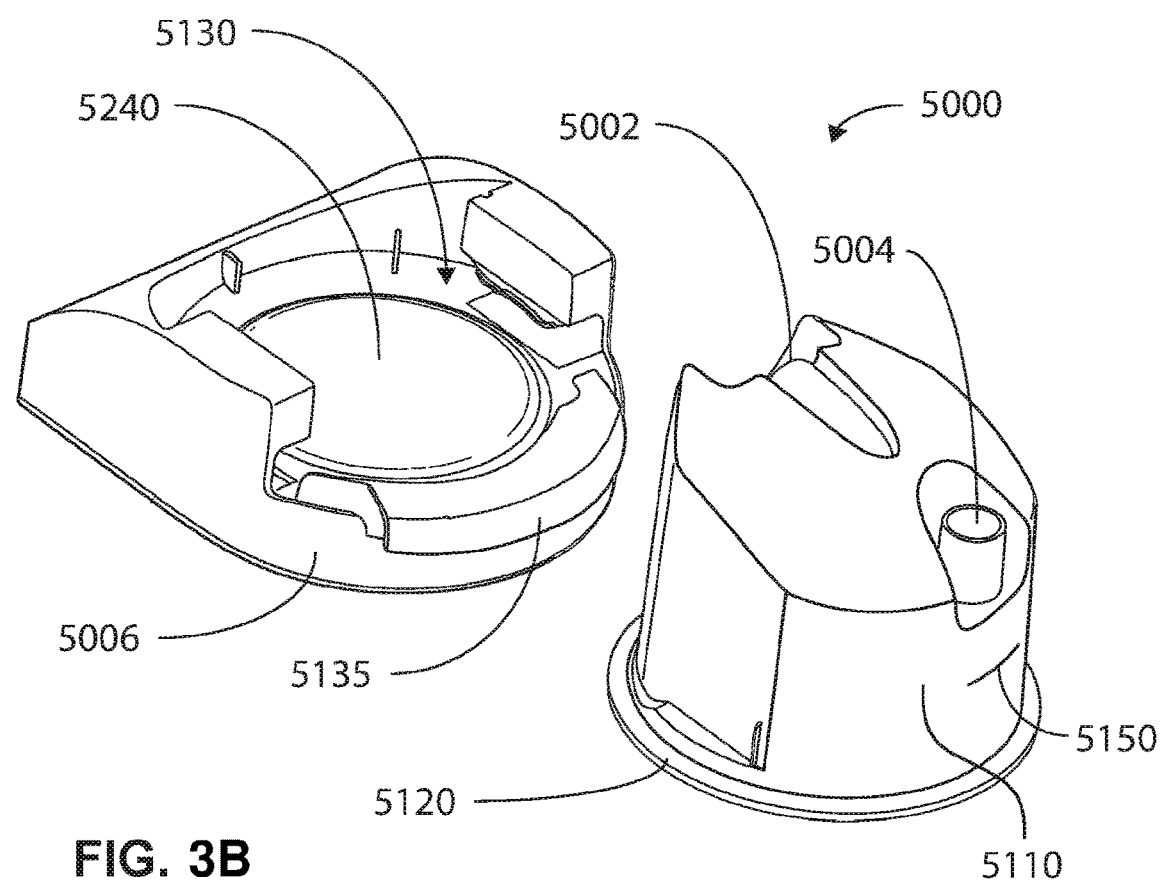

FIG. 3B shows an isometric view of a humidifier in accordance with one form of the present technology, showing a humidifier reservoir 5110 removed from the humidifier reservoir dock 5130.

Figure 3C:
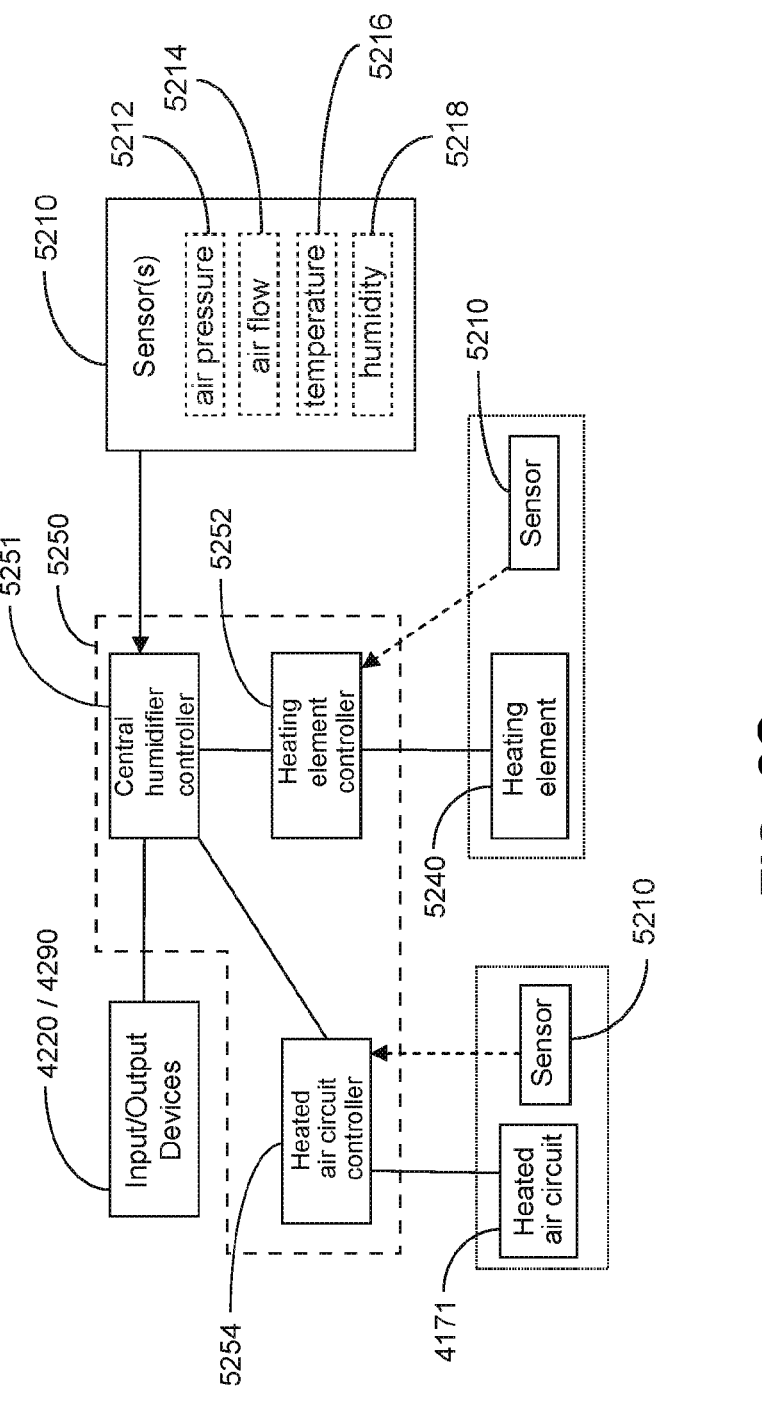

FIG. 3C shows a schematic of a humidifier in accordance with one form of the present technology.

Figure 3D:
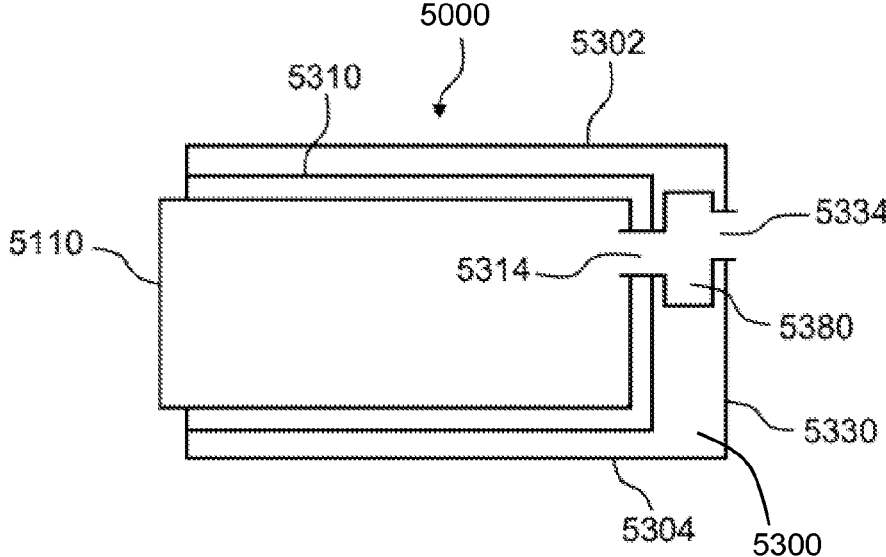

FIG. 3D shows a cross-sectional view of a humidifier in accordance with one form of the present technology.

Liquid Diversion Assembly

Figure 4A:
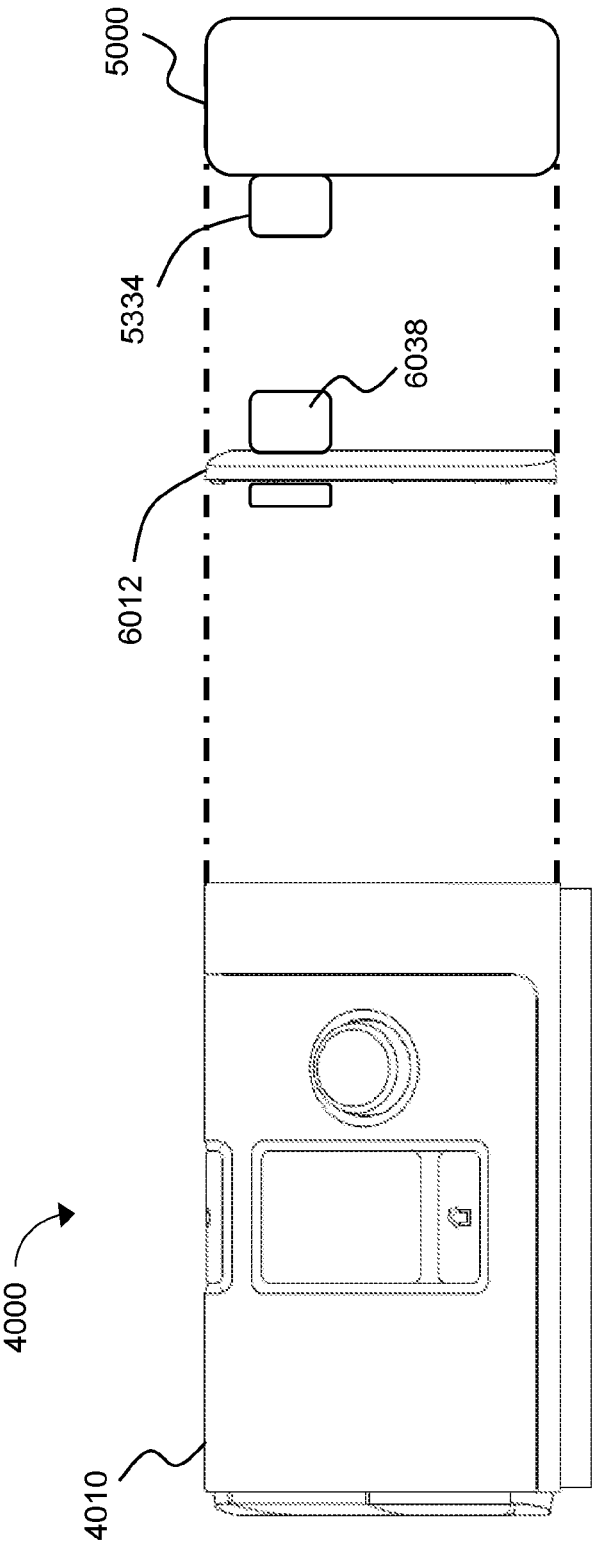

FIG. 4A shows an exploded isometric view of an RPT device in association with a liquid diversion assembly and further coupled to a humidifier, in accordance with one form of the present technology.

Figure 4B:
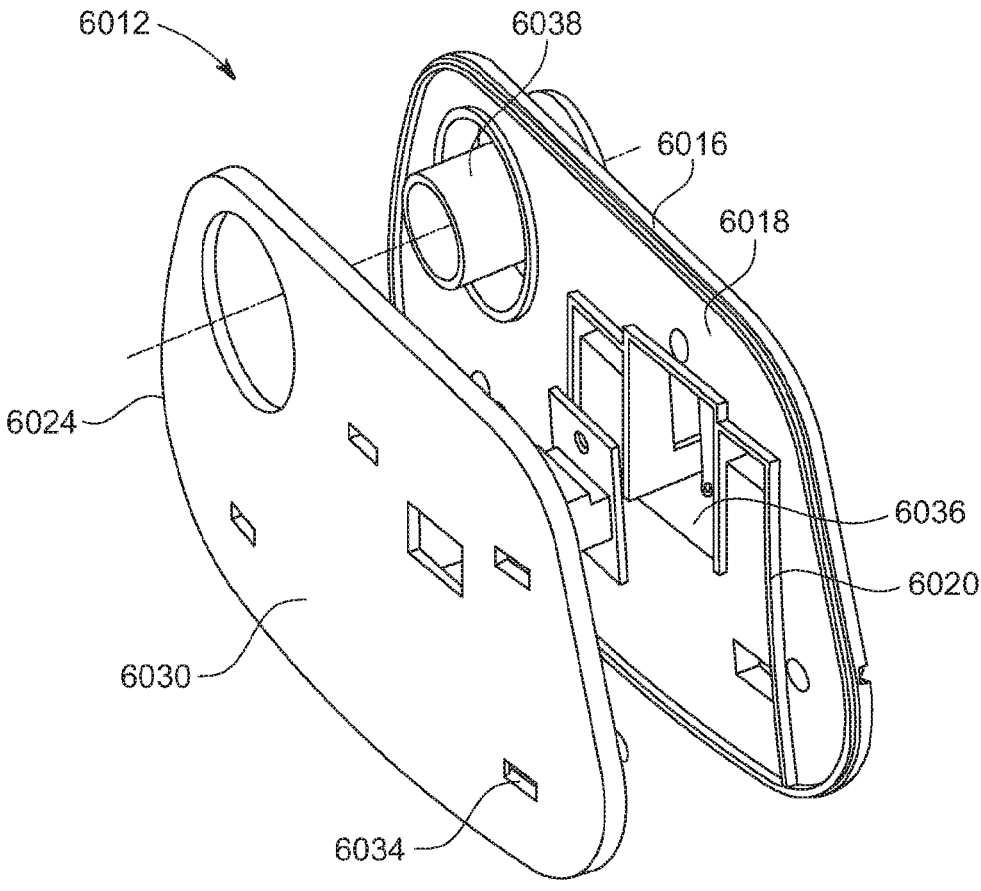

FIG. 4B shows an exploded isometric view of the liquid diversion assembly shown in FIG. 4A in accordance with one form of the present technology.

Figure 4C:
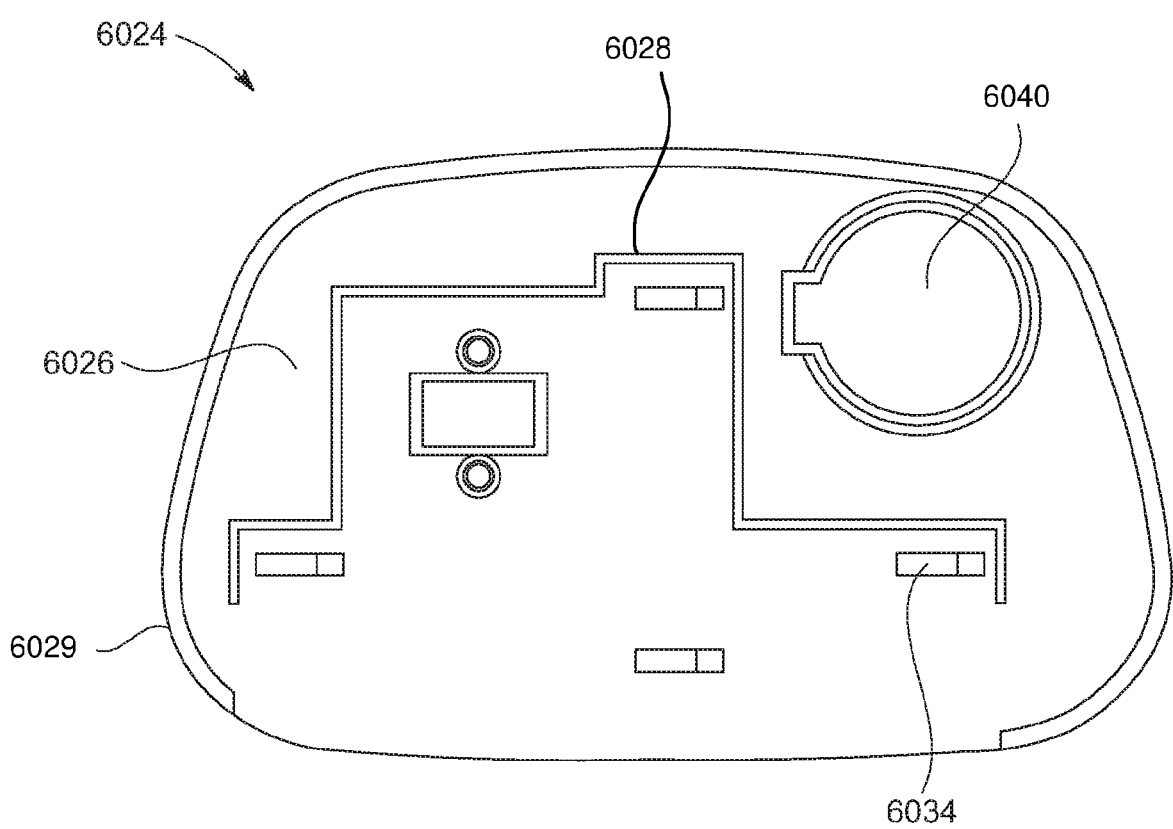

FIG. 4C shows an isometric view of the liquid diversion assembly of FIG. 4B, showing the interior surface of the distal panel.

Figure 4D:
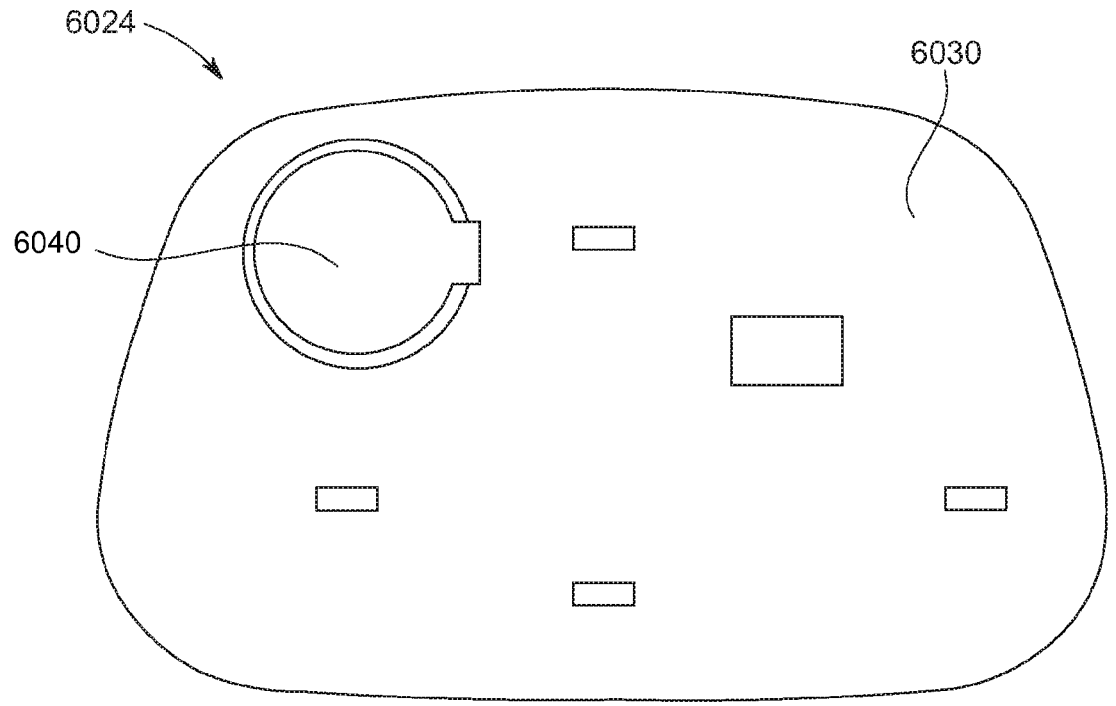

FIG. 4D shows an isometric view of the liquid diversion assembly of FIG. 4B, showing the exterior surface of the distal panel.

Figure 4E:
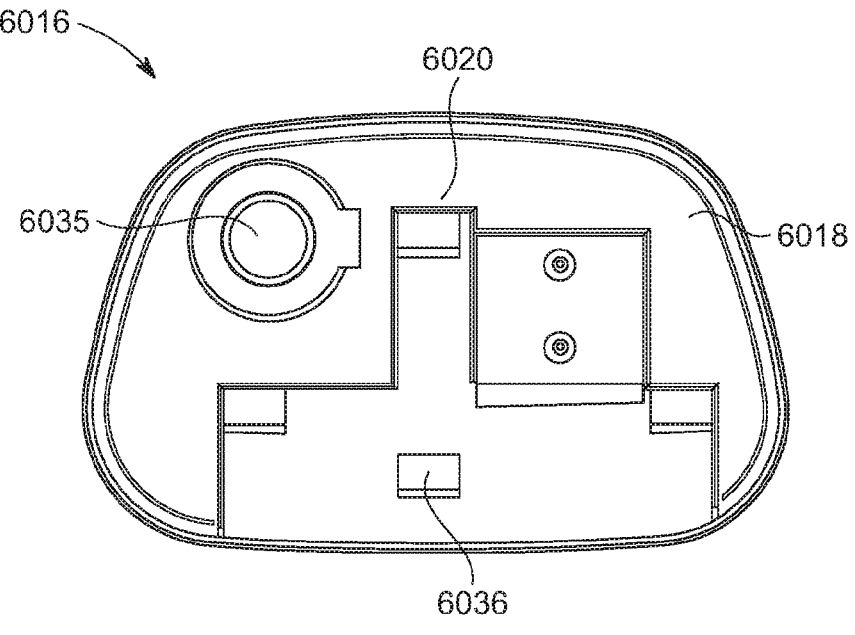

FIG. 4E shows an isometric view of the liquid diversion assembly of FIG. 4B, showing the interior surface of the proximal panel.

Figure 4F:
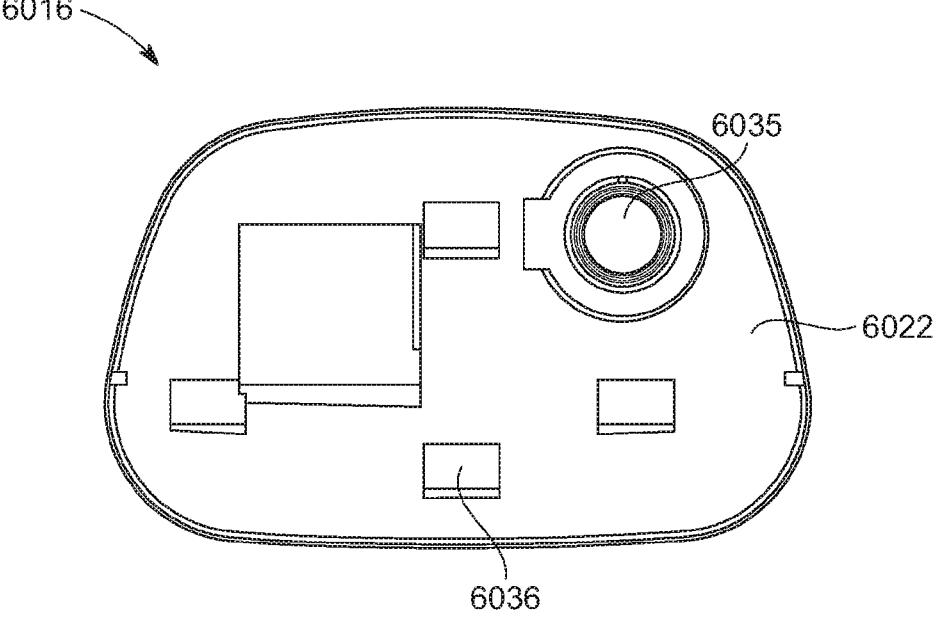

FIG. 4F shows an isometric view of the liquid diversion assembly of FIG. 4B, showing the exterior surface of the proximal panel.

Figure 4G:
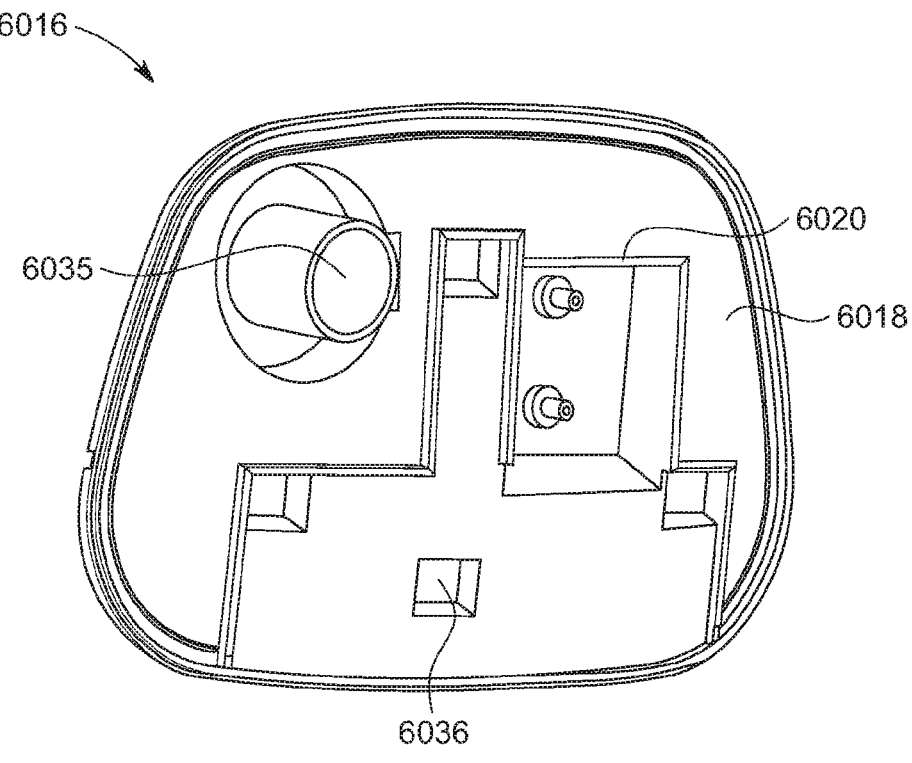

FIG. 4G shows an isometric view of the liquid diversion assembly of FIG. 4B, showing the interior surface of the proximal panel.

Figure 4H:
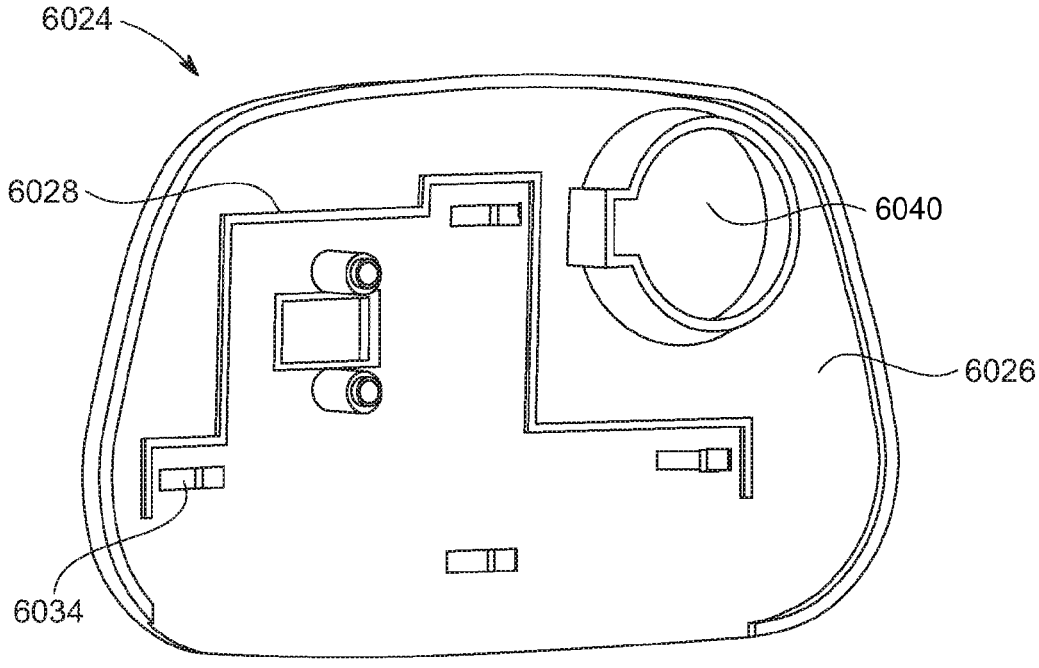

FIG. 4H shows an isometric view of the liquid diversion assembly of FIG. 4B, showing the interior surface of the distal panel.

Figure 4I:
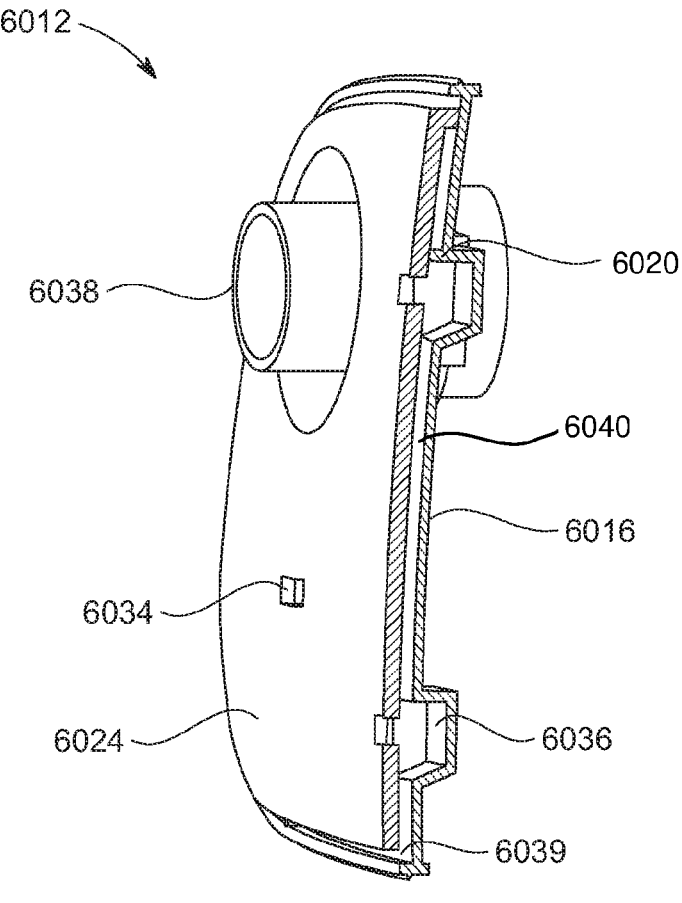

FIG. 4I shows a cross-sectional view of the liquid diversion assembly of FIG. 4B.

Figure 5A:
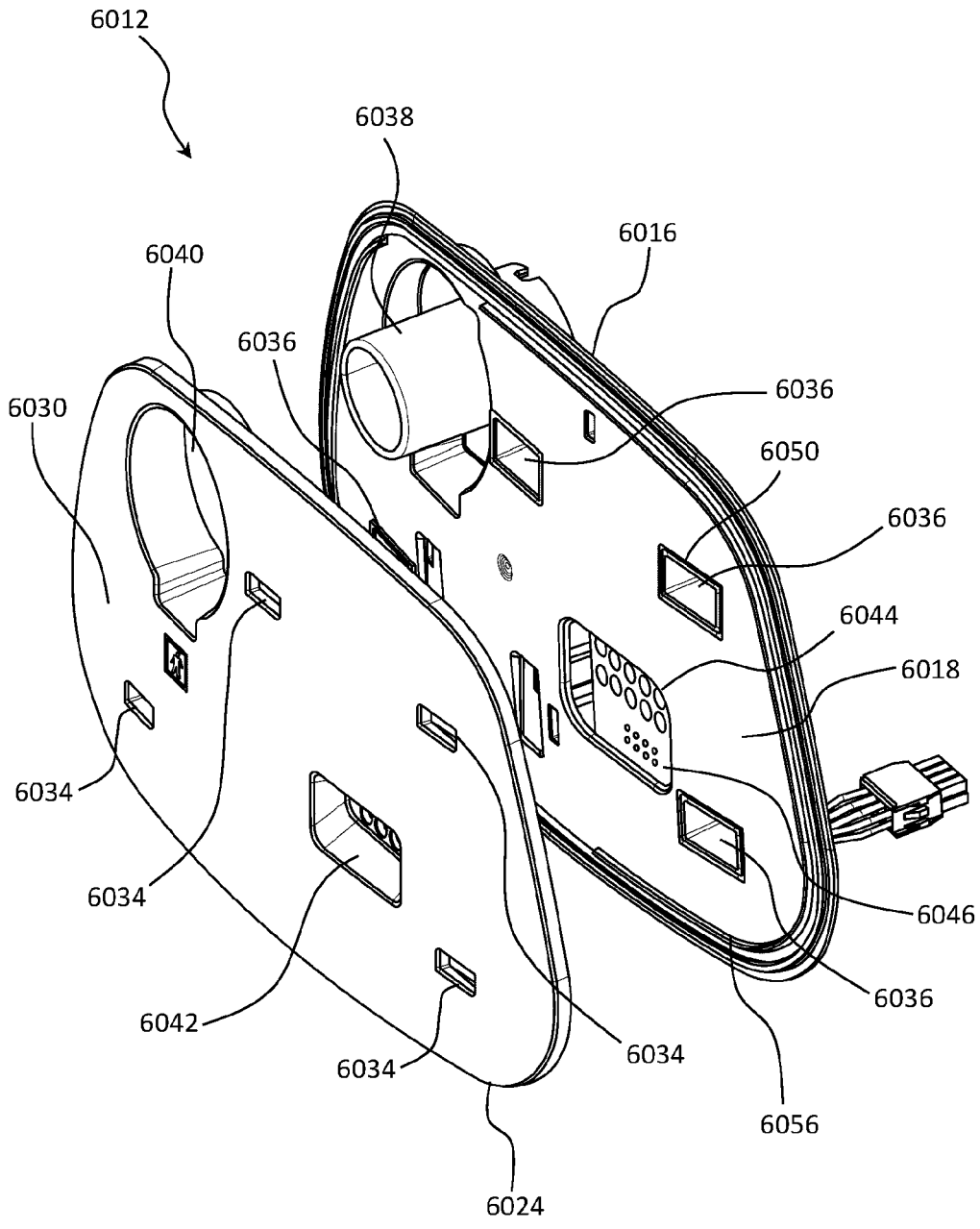

FIG. 5A shows an exploded isometric view of another example of a liquid diversion assembly in accordance with one form of the present technology.

Figures 5B, 5C:
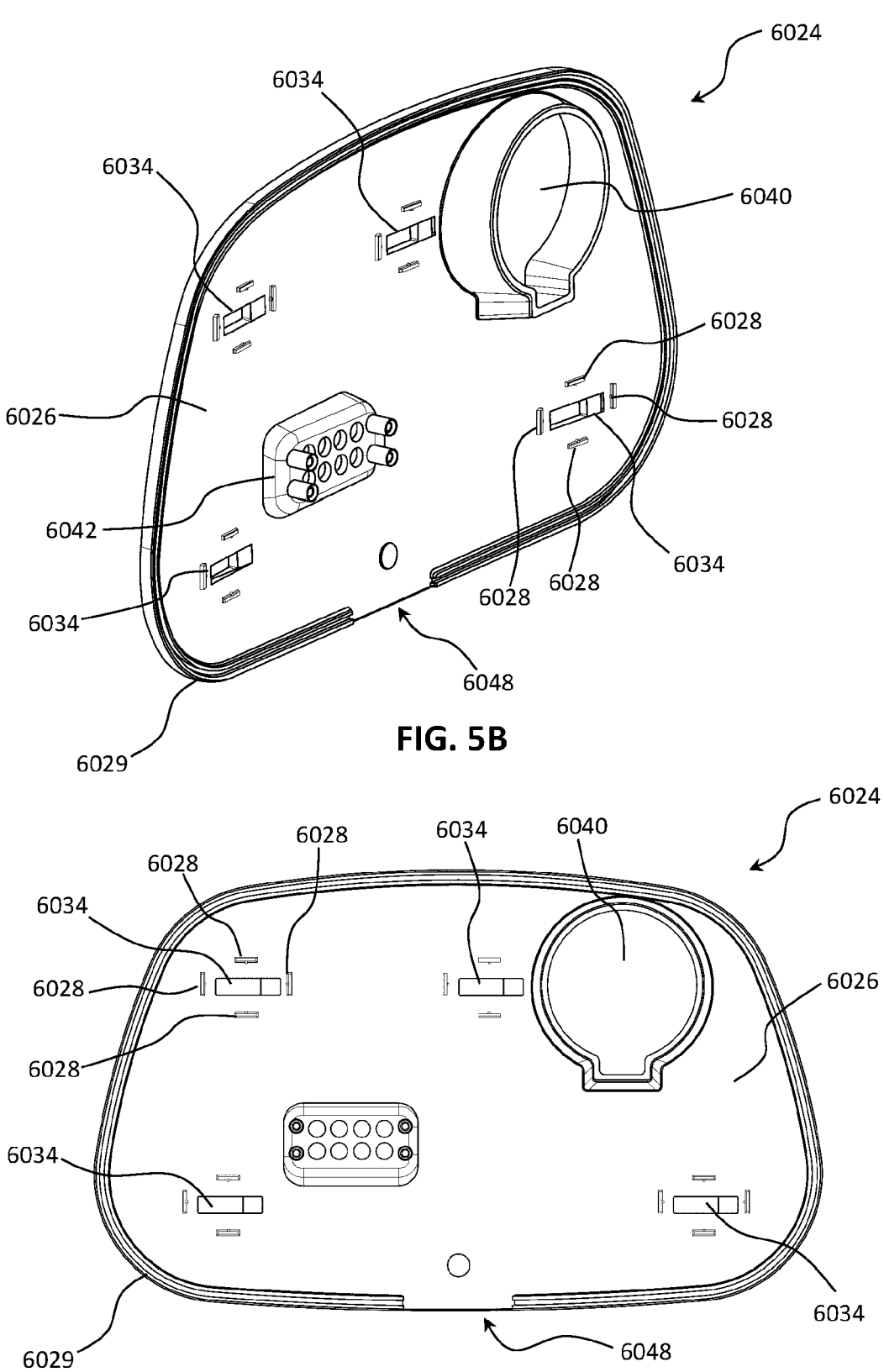

FIG. 5B shows an isometric view of the interior surface of a distal panel of the liquid diversion assembly.

FIG. 5C shows an end view of the interior surface of the distal panel of the liquid diversion assembly.

Figure 5D:
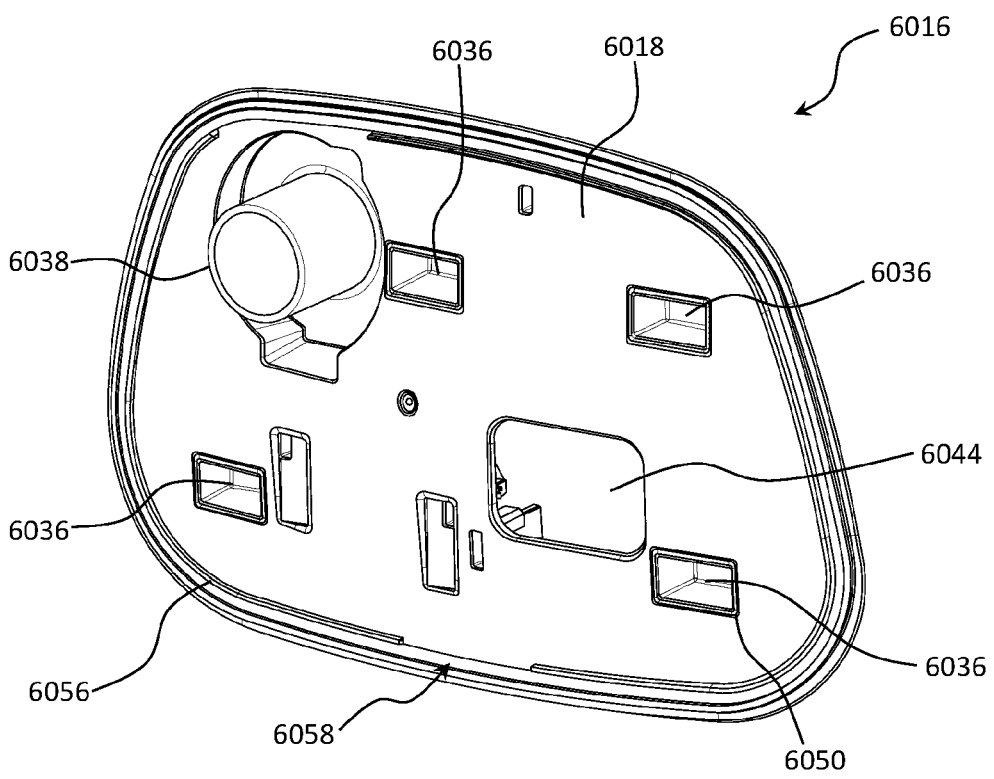

FIG. 5D shows an isometric view of the interior surface of a proximal panel of the liquid diversion assembly.

Figure 5E:
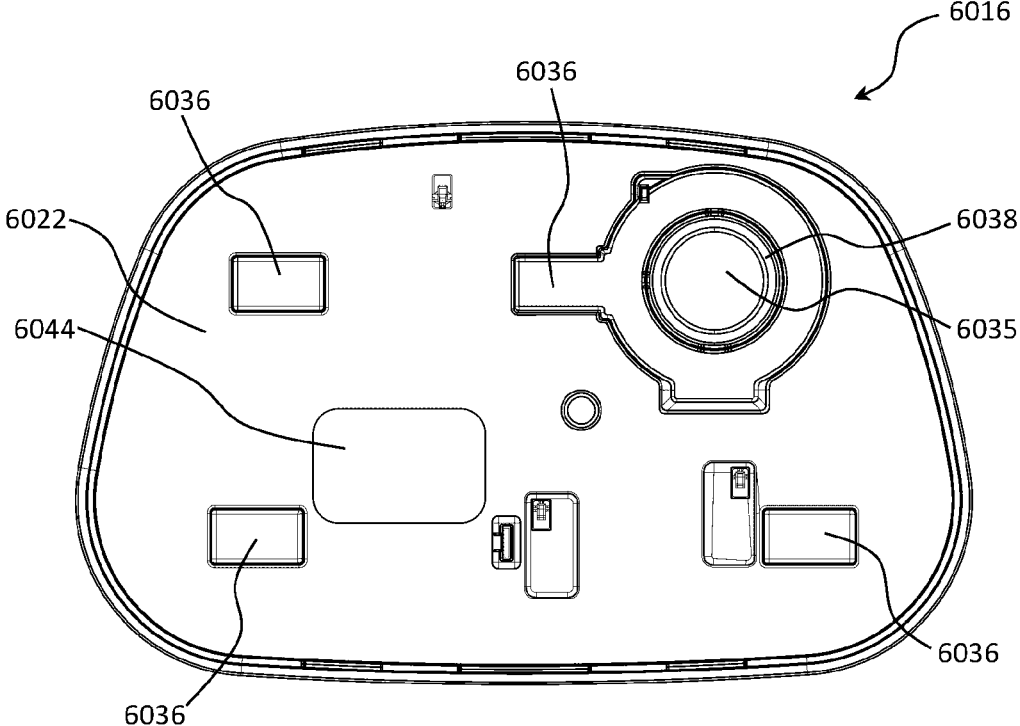

FIG. 5E shows an end view of the exterior surface of the proximal panel of the liquid diversion assembly.

Figure 5F:
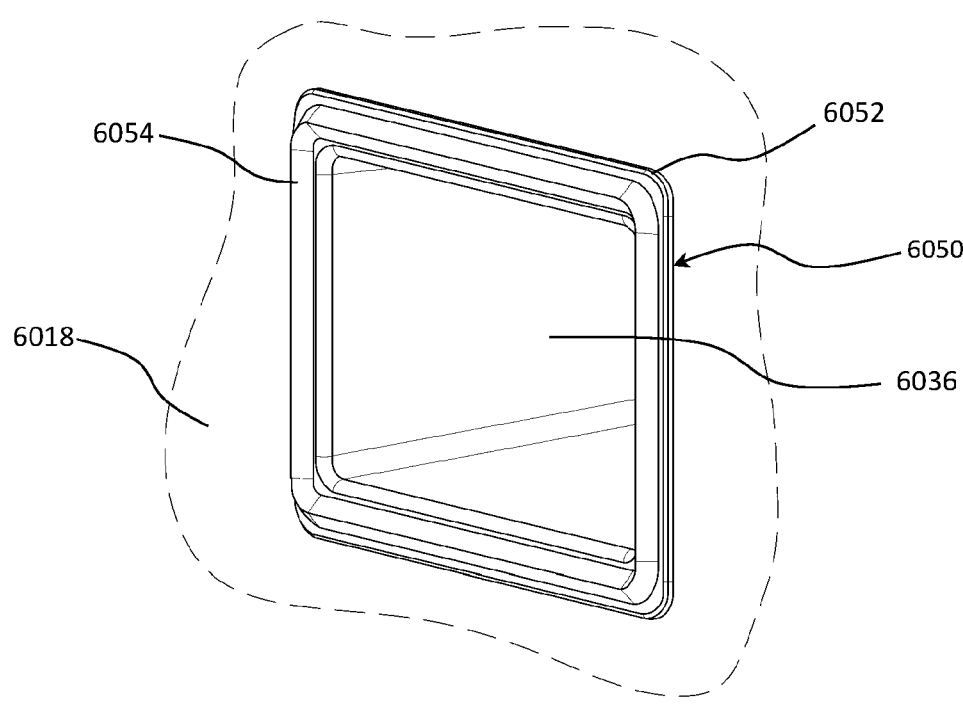

FIG. 5F shows an isometric view of a recess in the interior surface of the proximal panel of the liquid diversion assembly.

Figure 5G:
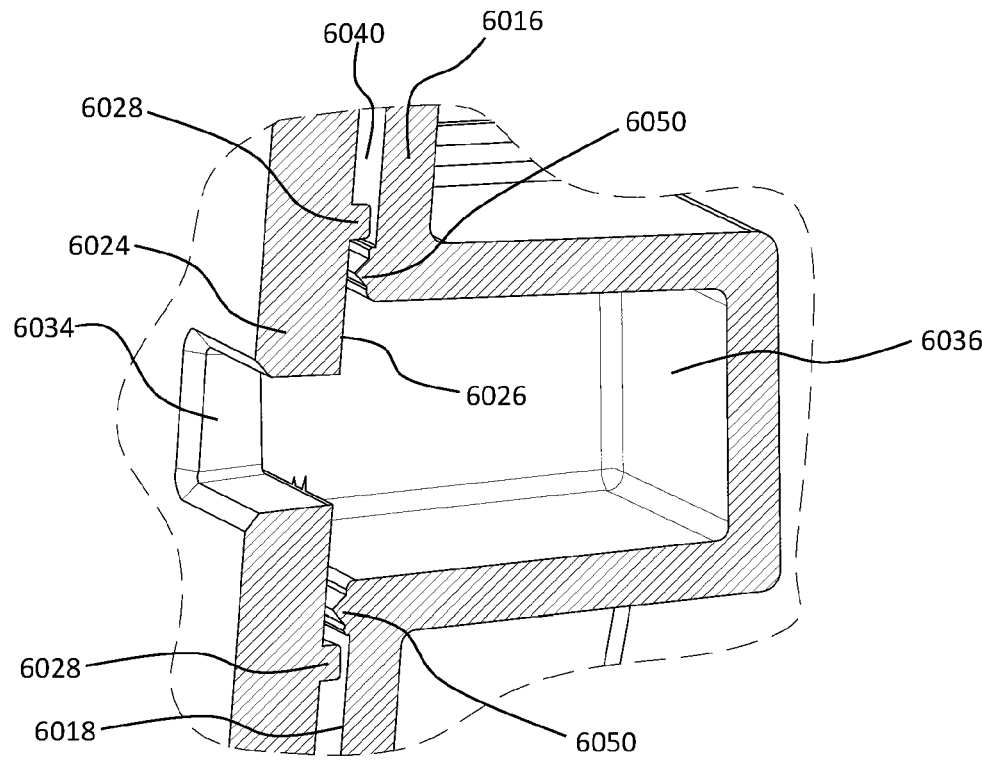

FIG. 5G shows a cross-sectional view of the recess in the interior surface of the proximal panel of the liquid diversion assembly.

Figure 5H:
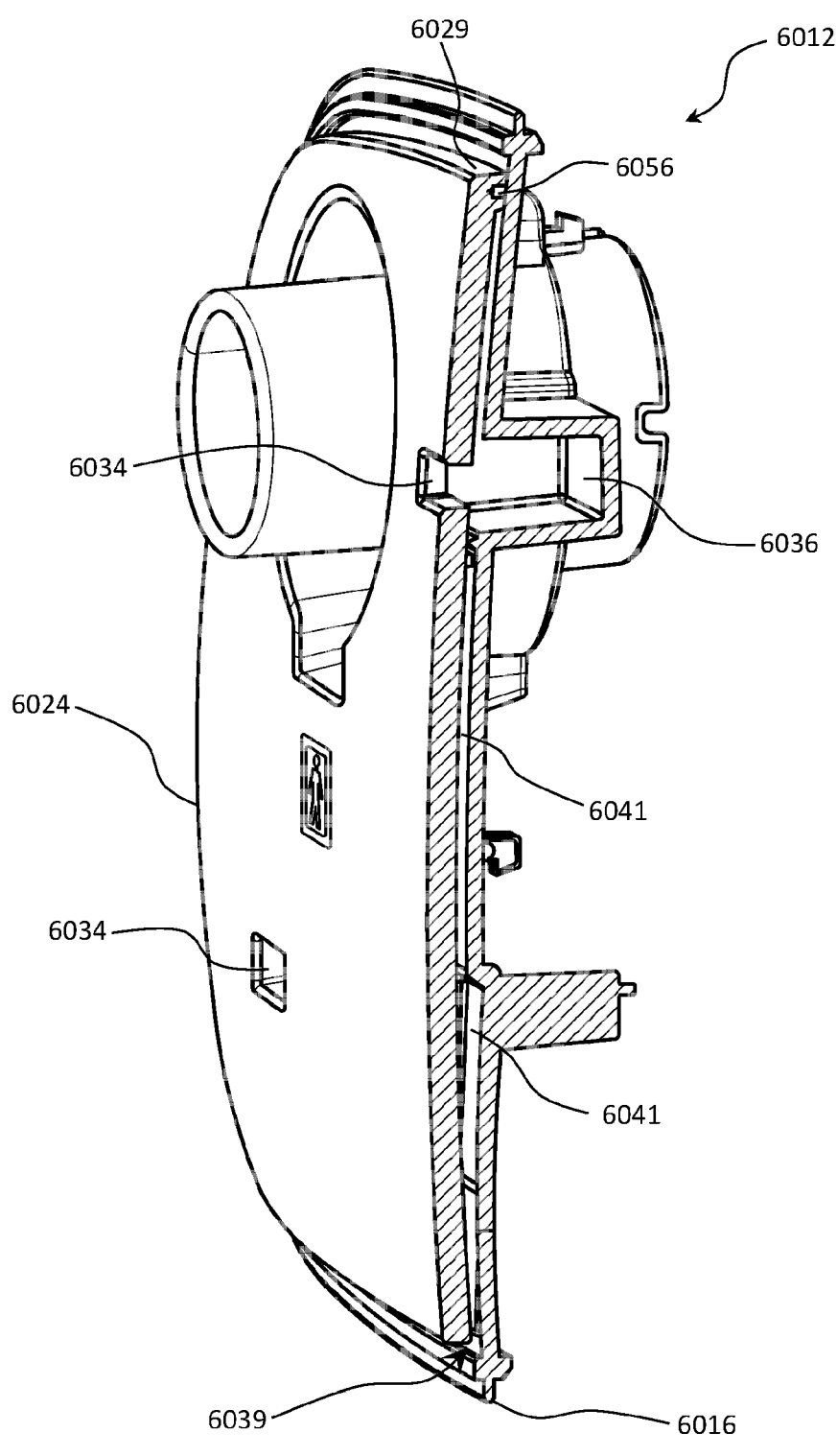

FIG. 5H shows a cross-sectional view of the liquid diversion assembly.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

Humidifier

Humidifier Overview

Respiratory humidifiers are available in many forms and may be a standalone device that is coupled to an RPT device via an air circuit, is integrated with the RPT device or configured to be directly coupled to the relevant RPT device.

While known passive humidifiers can provide some relief, generally a heated humidifier may be used to provide sufficient humidity and temperature to the air so that the patient will be comfortable. In examples, humidifiers comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with an RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

In one form of the present technology there is provided a humidifier 5000 (e.g. as shown in FIG. 3A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 3A and FIG. 3B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

Humidifier Components

Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 3A and FIG. 3B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

Humidifier Reservoir Dock

In one form, the humidifier 5000 may comprise a humidifier reservoir dock 5130 (as shown in FIG. 3B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

Water Level Indicator

The humidifier reservoir 5110 may comprise a water level indicator 5150 as shown in FIG. 3A-3B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 3C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

Pressure Transducer

One or more pressure transducers 5212 may be provided to the humidifier 5000 in addition to, or instead of, a pressure sensor 4272 provided in the RPT device 4000.

Flow Rate Transducer

One or more flow rate transducers 5214 may be provided to the humidifier 5000 in addition to, or instead of, a flow rate sensor 4274 provided in the RPT device 4000.

Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 3B.

Humidifier Controller

According to one arrangement of the present technology, a humidifier 5000 may comprise a humidifier controller 5250 as shown in FIG. 3C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 3C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

Liquid Ingress from Humidifier

According to one aspect of the present technology, a humidifier 5000 may have a body comprising an external housing 5300. In one example, the housing 5300 may be formed in two parts, an upper portion 5302 and a lower portion 5304. The body of humidifier 5000 further comprises a chassis 5310.

Reference to a chassis herein should be understood to mean a supporting frame of a structure—i.e. a structural element configured to support one or more other components, more particularly one or more internal components of the humidifier 5000. Reference to a housing should be understood to mean an element that covers or protects other components of a structure. In one example the housing 5300 is provided to at least partially cover or protect the chassis 5310. In alternative examples, the humidifier 5000 may comprise a housing 5310 configured to act as a chassis 5310. In alternative examples, the humidifier 5000 may comprise a chassis 5310 without a separate housing per se.

In examples, the humidifier 5000 comprises a removable container in the form of water reservoir 5110. The chassis 5310 is configured to locate and support the removable reservoir 5110 in use. In the example shown in FIG. 3D, the reservoir 5110 is inserted and removed from an end of the humidifier. In alternative examples, the reservoir 5110 may be removed from a side of the humidifier 5000 (i.e. laterally), or from above or below (i.e. vertically). PCT Patent Application Publication No. WO 2018/094452 A1 describes exemplary arrangements for a humidifier having a removable water reservoir, the contents of which are incorporated herein by reference in their entirety.

In alternative examples, the chassis 5310 may comprise a chamber which functions as the water reservoir 5110—i.e. is integrated with the chassis 5310 rather than being removable.

There are various circumstances in which water may pass through the chamber inlet port 5314 from the reservoir 5110, including knocking of the humidifier 5000 or a stand on which it sits to produce a sloshing effect, or tipping of the humidifier 5000 as it is shifted or re-oriented.

According to one aspect of the present technology, as shown in FIG. 3D, the humidifier 5000 comprises a closure element in the form of a chassis cap 5330. In this example the chassis cap 5330 is configured to seal against the humidifier housing 5300 and the humidifier chassis 5310, as described further below.

In examples, the chassis cap 5330 comprises an air inlet port 5334 configured to be connected to a source of a flow of air at positive pressure, for example RPT device 4000.

In examples, there is provided a gas flow path between the air inlet port 5334 and the chamber inlet port 5314, which in some configurations forms a liquid trap 5380 for retention of a volume of water spilled through the chamber inlet port 5314.

There are various circumstances in which water may pass through the chamber inlet port 5314 from the reservoir 5110, including knocking of the humidifier 5000 or a stand on which it sits to produce a sloshing effect, or tipping of the humidifier 5000 as it is shifted or re-oriented. The liquid trap 5380 is provided to retain a volume of this spilled water to reduce the likelihood of water reaching other components of the system upstream, more particularly the RPT device 4000.

An advantage of the liquid diversion assembly embodiments described herein is that they provide a simple, cost effective and user friendly mechanism to prevent damage to the RPT device which may result from such "sloshing" or "tipping" of the humidifier that causes liquid to flow from the reservoir 5110 via the chamber inlet port 5314 and into the pneumatic block 4020 which houses the motor 4144 and various sensors, along with electrical supply. This flow of liquid may be via either direct sloshing, or through leak in the non-watertight connections in the air inlet path 5334, or both.

Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH₂O, or at least 10cmH₂O, or at least cmH₂O.

The RPT device may have an external housing 4010, formed in two parts, an upper portion 4012 and a lower portion 4014. Furthermore, the external housing 4010 may comprise one or more panel(s) 4015. The RPT device 4000 comprises a chassis 4016 that supports one or more internal components of the RPT device 4000. The RPT device 4000 may comprise a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of, the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

RPT Device Mechanical & Pneumatic Components

An RPT device may comprise one or more of the following components in an integral unit. In an alternative form, one or more of the following components may be located as respective separate units.

Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH₂O to about 20 cmH₂O, or in other forms up to about 30 cmH₂O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 is received by the central controller 4230.

Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

Liquid Diversion Assembly

According to one form of the present technology, as shown in FIG. 4A, the housing 4010 comprises a closure element in the form of an end cap 6012. In this example the end cap 6012 is configured to seal against the housing 4010 and can selectively be coupled to a compatible medical device, such as a humidifier 5000, as described further below.

In one form as best shown in FIG. 4B, the end cap 6012 comprises at least one coupling component 6038 comprising a gas aperture 6035 configured to be in fluid communication with the outlet of the pneumatic block 4020 in use, at least one aperture 6034, at least one recess 6036, where the at least one aperture 6034, recess 6036 and coupling component 6038 are configured such that they may facilitate selective connection to a humidifier 5000. In other forms of the present technology there are multiple possible embodiments of the outer portion comprising different configurations of one or more of the apertures 6034, coupling component 6038, and/or recess 6036 (for example, as illustrated in the exemplary end cap 6012 shown in FIG. 5A).

In one form of the present technology, the end cap 6012 comprises at least one internal channel in fluid communication with at least one aperture 6034 (also referred to herein as an internal fluid passageway) to divert liquid which has been "spilled" from a selectively connected humidifier 5000, or alternatively liquid which has been accidentally spilled onto the RPT device by a user, to the exterior of the housing 4010. In further forms end cap 6012 may comprise a plurality of internal channels to divert liquid from a plurality of apertures, coupling components, or recesses and can be configured in a variety of forms depending on the nature of the selective compatible accessory or medical device. The end cap 6012 is therefore referred to herein as a liquid diversion assembly.

In one form the end cap 6012 may be constructed from a plurality of panels, for example proximal panel 6016, and distal panel 6024. Each panel will be referred to as having an interior surface (e.g. surfaces 6018, and 6026 respectively) and exterior surfaces (e.g. surfaces 6022, and 6030 respectively). These panels 6016, 6024 may be assembled such that during operational orientation the proximal panel 6016 sits proximal to the electrical components of the medical device 4000, and distal panel 6024 sits distal to the electrical components of the medical device 4000 (i.e. closer to the humidifier 5000 when selectively coupled to same). These panels 6016, 6024 may be joined mechanically, thermally or ultrasonically bonded to form the end cap 6012. In alternate forms one or more additional panels may be included in the end cap 6012. In further alternate forms a single panel may be constructed with a similar internal configuration to that described herein (i.e. the provision of the one or more internal channels), such as through moulding or 3D printing methods.

In one form of the present technology there is provided a proximal panel 6016 comprising an interior surface 6018 configured to comprise at least one protrusion forming a guide wall 6020. The guide wall 6020 may project from the interior surface 6018 of the panel 6016 at a substantially perpendicular angle, however other angles of protrusion may also be suitable. The proximal panel 6016 may further comprise at least one recess 6036. In use, such recesses 6036 may receive fastening elements of the humidifier 5000 (for example, barbed latches configured to be inserted through apertures 6034 and catch on interior surface 6026 of the distal panel 6024), or components of an electrical connector (for example, a PCB assembly connected to a wiring loom, to which a complementary electrical connector may be coupled). In such examples the at least one protrusion forming a guide wall 6020 may extend from positions in association with the area defined by the at least one recess 6036. In some forms, the at least guide wall 6020 may comprise one or more superior portions extending along the interior surface 6018 in a position superior to the at least one recess 6036, when the end cap 6012 is in an operational, or in-use, orientation. In some forms, the at least guide wall 6020 may comprise one or more lateral portions extending along the interior surface 6018 in a position to the side of the at least one recess 6036. In examples, such as shown in FIG. 4E, the lateral portions may connect between two superior portions. In some forms, the at least one guide wall 6020 may substantially surround the at least one recess 6036. In some forms the at least one guide wall 6020 extends beyond the perimeter of the at least one recess 6036, for example to connect with the perimeter of the panel 6016.

In some forms of the current technology the at least one guide wall 6020 may be moulded from the same material as the proximal panel 6016, however it is also contemplated that the guide wall 6020 may be formed from a flexible material such as silicone or alternatively constructed from a hydrophobic membrane.

In one form the end cap 6012 may comprise a distal panel 6024 distal to the medical device 4000. The distal panel 6024 may comprise a coupling aperture 6040 configured to receive the coupling component 6038—for example shaped to key to the surround of the coupling component 6038. The distal panel 6024 may comprise an interior surface 6026 configured to comprise at least one protrusion providing a locating feature 6028. The at least one locating feature 6028 may extend at a substantially perpendicular angle to the interior surface 6026 of the panel 6024. The distal panel 6024 may further comprise at least one aperture 6034 between interior surface 6026 and exterior surface 6030. The at least one locating feature 6028 may extend from positions in association with the area defined by the at least one aperture 6034. In some forms the locating feature 6028 may substantially surround the at least one aperture 6034.

In examples, distal panel 6024 may further comprise a perimeter wall 6029. The perimeter wall 6029 may extend at a substantially perpendicular angle to the interior surface 6026 of the panel 6024 along at least a portion of the perimeter of the panel 6024. In examples the perimeter wall 6029 may extend along the interior surface 6026 of the panel 6024 in a position radially outward of the apertures 6034. In examples the perimeter wall 6029 may extend along the interior surface 6026 of the panel 6024 in a position radially outward of the at least one guide wall 6034. In examples a portion of the perimeter wall 6029 may extend along the interior surface 6026 of the panel 6024 in a position superior to the at least one guide wall 6020. In examples a portion of the perimeter wall 6029 may extend along the interior surface 6026 of the panel 6024 in a position laterally offset from the at least one guide wall 6020 (i.e. to a side of the guide wall(s) 6020).

In operation, liquid may penetrate the RPT device 4000 in a multitude of ways. In the event of a user accidentally tipping or sloshing liquids over the device, liquid ingress can occur at the perimeter of the end cap 6012 or, if used without a coupled humidifier, via the one of more apertures 6034 and recesses 6036. When coupled with a humidifier 5000, liquid can flow from the reservoir 5110 (for example, via the non-watertight connectors that cooperate with one or more apertures 6034). In the event of liquid penetrating the device either at the perimeter of the end cap 6012 or from the humidifier 5000 via the non-watertight connectors, some forms of the present technology provide an end cap 6012 comprising a plurality of panels 6016, 6024. The panels 6016 and 6024 are configured such that when the proximal 6016 and distal 6024 panels are connected into an end cap 6012, the interior surfaces 6018 and 6026, and at least one the guide wall 6020 cooperate to form at least one internal fluid passageway 6041 within the end cap 6012, as illustrated in the cross-sectional view of FIG. 4I. In examples, the locating feature(s) 6028 may co-operate with the least one the guide wall 6020 to provide a watertight seal. In alternative examples, the locating feature(s) 6028 may function to interact with the guide wall(s) 6020 to locate the panels 6016 and 6024 relative to each other, with sealing occurring between the guide wall(s) 6020 and the internal surface 6026 of the distal panel 6024.

In the example of FIG. 4B to FIG. 4I, the internal fluid passageway 6041 has a watertight perimeter confining liquid ingressed from the apertures 6034 and recesses 6036, and acts as a channel to diverts any ingressed liquid towards the lower, or inferior, portion of the end cap 6012, where there is a gap 6039 in the watertight perimeter through which the liquid can escape to the outside surface of the RPT device housing 4010 as a result of gravity, capillary action, or other natural force. The ingressed liquid is thus diverted from the sensitive electrical components of the RPT device 4000, described below. The lower surface of one or more of the recesses 6036 may also be cambered (or more generally angled from a superior position to an inferior position at the interior surface 6018), as illustrated in FIG. 4I, so that any ingressed liquid does not collect in the recess 6036, but flows out of it by the action of gravity, and through the internal fluid passageway 6041 towards the lower portion of the end cap 6012.

In some examples, one or more of the surfaces forming the fluid passageway is coated in a hydrophobic material to facilitate faster diversion of liquid to the exterior of the housing 4010.

While the exemplary end cap 6012 of FIG. 4B to FIG. 4I has been described with reference to the guide wall 6020 being provided on the interior surface 6018 of the proximal panel 6016, and the locating feature(s) 6028 and perimeter wall 6029 being provided on the interior surface 6026 of the distal panel 6024, it should be appreciated that in alternative examples an inverse arrangement, or a combination thereof, may be utilised to provide the internal fluid passageway(s).

FIG. 5A shows another example of a closure element in the form of an end cap 6012 according to an aspect of the present technology. In this example the end cap 6012 is configured to be selectively coupled to a compatible medical device, such as humidifier 5000, to seal against the housing 4010 of same. As generally described above, the end cap 6012 is configured to facilitate selective connection to a humidifier 5000.

In this example the end cap 6012 comprises a proximal panel 6016 having an interior surface 6018 and an exterior surface 6022, and a distal panel 6024 having an interior surface 6026 and an exterior surface 6030. In this example, the distal panel 6024 comprises an electrical connector recess 6042 in exterior surface 6030 (i.e. projecting from interior surface 6026. The proximal panel 6016 comprises an electrical connector aperture 6044, through which the electrical connector recess 6042 projects, with electrical connector PCB assembly 6046 mounted to standoffs of the electrical connector recess 6042 on the exterior side of the proximal panel 6016. In use, an electrical connector is inserted into the electrical connector recess 6042 and interfaces with a corresponding connector coupled to the PCB assembly 6046.

In this example, the distal panel 6024 comprises a plurality of apertures 6034. On the interior surface 6026 of the distal panel 6024, a plurality of locating features 6028 are provided about each aperture 6034, extending at a substantially perpendicular angle to the interior surface 6026 of the panel 6024. In examples locating features 6028 may be provided in superior and/or inferior positions relative to each aperture 6034. In examples the length of locating features 6028 in superior and/or inferior positions, across the interior surface 6026 (i.e. in a lateral direction), may be less than the width of an associated aperture 6034. In examples locating features 6028 may be provided in one or more lateral positions relative to each aperture 6034 (i.e. to one or more sides of the aperture 6034). In the example shown (see, e.g. FIG. 5C), the locating features 6028 are discrete—i.e. not connected to each other, having gaps therebetween.

In examples, distal panel 6024 may further comprise a perimeter wall 6029. The perimeter wall 6029 may extend at a substantially perpendicular angle to the interior surface 6026 of the panel 6024 along at least a portion of the perimeter of the panel 6024. In the illustrated example (see, e.g. FIG. 5C) the perimeter wall 6029 extends around the perimeter of the panel 6024, having a perimeter wall gap 6048 in a location inferior to the apertures 6034.

In this example (see, e.g. FIG. 5D) the proximal panel 6016 comprises guide protrusions 6050 projecting from the interior surface 6018 of the panel 6016. In this example, the guide protrusions 6050 surround each of the recesses 6036. Referring to FIG. 5F, in this example the guide protrusions 6050 comprise a raised base 6052, and a guide projection 6054 extending from the raised base 6052. In this example, the guide projection 6054 has a radially outward facing surface and a radially inward facing surface tapering towards each other to meet at a pointed apex—although it should be appreciated that in alternative examples the apex may be rounded, or flat. In this example, a plateau portion is provided between a radially outward edge of the raised base 6052 and the guide projection 6054. In alternative examples, the guide projection 6054 may extend directly from the interior surface 6018 (i.e. the guide protrusion 6050 may not comprise a raised base 6052).

Referring to FIG. 5D, in this example the proximal panel 6016 comprises a locating wall 6056 projecting from the interior surface 6018 of the panel 6016. The locating wall 6056 extends along the interior surface 6018 in a radially outward position relative to the recesses 6036, aligning with the perimeter wall 6029 of the distal panel 6024 when formed as the end cap 6012. The locating wall 6056 also comprises a locating wall gap 6058, substantially aligned with the perimeter wall gap 6048 of the of the distal panel 6024.

Referring to FIG. 5G and FIG. 5H, when the end cap 6012 is formed by joining of the proximal panel 6016 and the distal panel 6024, an internal fluid passageway 6041 is formed therebetween. The perimeter wall 6029 and locating wall 6056 cooperate to form a seal around the periphery of the internal fluid passageway 6041, more particularly extending around the surfaces comprising apertures 6034 and recesses 6036 collectively, with the exception of gap 6039 produced by the locating wall gap 6058 and the perimeter wall gap 6048 at an inferior position. In this example, the seal extends around the periphery of the coupling component 6038 and coupling aperture 6040. Liquid entering the internal fluid passageway 6041 is permitted to flow through to the exterior of the end cap 6012 via the gap 6039. With particular reference to FIG. 5G, in this example liquid moving downwards towards a recess 6036, or flowing from the recess 6036, is encouraged by the shaped surfaces of the guide protrusion 6050 to move towards the interior surface 6026 and flow down the internal fluid passageway 6041 towards the gap 6039.

RPT Device Electrical Components

Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

Clock

The RPT device 4000 may include a clock 4232 that is connected to the central controller 4230.

Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

Protection Circuits

The one or more protection circuits 4250 in accordance with the present technology may comprise an electrical protection circuit, a temperature and/or pressure safety circuit.

Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

Display Driver

A display driver 4292 receives as an input the characters, symbols, or images intended for display on the display 4294, and converts them to commands that cause the display 4294 to display those characters, symbols, or images.

Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to a patient interface.

Glossary

For the purposes of the present technology disclosure, in certain forms of the present technology, one or more of the following definitions may apply. In other forms of the present technology, alternative definitions may apply.

General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air or liquid.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. The outward normal vector at p points away from the surface. In some examples we describe the surface from the point of view of an imaginary small person standing upright on the surface.

Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). Such curves are often referred to as concave.

Zero curvature: If the curve at p is a straight line, the curvature will be taken to be zero (if the imaginary small person leaves the point p, they can walk on a level, neither up nor down).

Negative curvature: If the curve at p turns away from the outward normal, the curvature in that direction at that point will be taken to be negative (if the imaginary small person leaves the point p they must walk downhill).

Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small.

Principal curvatures and directions: The directions of the normal planes where the curvature of the curve takes its maximum and minimum values are called the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

Holes

A surface may have a one-dimensional hole, e.g. a hole bounded by a plane curve or by a space curve. Thin structures (e.g. a membrane) with a hole, may be described as having a one-dimensional hole.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit.

OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 6.8 REFERENCE SIGNS LIST | |
| --- | --- |
| patient | 1000 |
| bed partner | 1100 |
| RPT device | 4000 |
| external housing | 4010 |
| upper portion | 4012 |
| lower portion | 4014 |
| Panel | 4015 |
| Chassis | 4016 |
| Handle | 4018 |
| pneumatic block | 4020 |
| air filter | 4110 |
| inlet air filter | 4112 |
| outlet air filter | 4114 |
| Muffler | 4120 |
| inlet muffler | 4122 |
| outlet muffler | 4124 |
| pressure generator | 4140 |
| Blower | 4142 |
| Motor | 4144 |
| anti - spill back valve | 4160 |
| air circuit | 4170 |
| supplemental oxygen | 4180 |
| electrical components | 4200 |
| Printed Circuit Board Assembly (PCBA) | 4202 |
| electrical power supply | 4210 |
| input devices | 4220 |
| central controller | 4230 |
| clock | 4232 |
| therapy device controller | 4240 |
| protection circuits | 4250 |
| memory | 4260 |
| transducers | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |

-continued

| 6.8 REFERENCE SIGNS LIST | |
| --- | --- |
| local external device | 4288 |
| output devices | 4290 |
| display driver | 4292 |
| display | 4294 |
| algorithms | 4300 |
| pre-processing module | 4310 |
| interface pressure estimation algorithm | 4312 |
| vent flow rate estimation | 4314 |
| leak flow rate estimation | 4316 |
| respiratory flow rate estimation | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| methods | 4340 |
| humidifier | 5000 |
| humidifier inlet | 5002 |
| humidifier outlet | 5004 |
| humidifier base | 5006 |
| Reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| heating element | 5240 |
| humidifier controller | 5250 |
| central humidifier controller | 5251 |
| heating element controller | 5252 |
| air circuit controller | 5254 |
| upper portion | 5302 |
| lower portion | 5304 |
| chassis | 5310 |
| chamber inlet port | 5314 |
| chassis cap | 5330 |
| air inlet port | 5334 |
| liquid trap | 5380 |
| end cap | 6012 |
| proximal panel | 6016 |
| proximal panel interior surface | 6018 |
| guide wall | 6020 |
| proximal panel exterior surface | 6022 |
| distal panel | 6024 |
| distal panel interior surface | 6026 |
| locating feature | 6028 |
| perimeter wall | 6029 |
| distal panel exterior surface | 6030 |
| aperture | 6034 |
| gas aperture | 6035 |
| recess | 6036 |
| coupling component | 6038 |
| gap | 6039 |
| coupling aperture | 6040 |
| internal fluid passageway | 6041 |
| electrical connector recess | 6042 |
| electrical connector aperture | 6044 |
| electrical connector PCB assembly | 6046 |
| perimeter wall gap | 6048 |
| guide protrusions | 6050 |
| raised base | 6052 |
| guide projection | 6054 |
| locating wall | 6056 |
| locating wall gap | 6058 |

The invention claimed is:

1. A liquid diversion assembly for a medical device that includes a housing, the liquid diversion assembly comprising:

an end cap in association with the housing, the end cap comprising:

a proximal panel proximal to the medical device in use, comprising a first interior surface and a first exterior surface;

a distal panel distal to the medical device in use, comprising a second interior surface and a second exterior surface;

at least one wall extending between the first interior surface and the second interior surface;

at least one aperture for selective coupling with a compatible accessory, wherein the at least one aperture is between the second exterior surface and the second interior surface of the distal panel, wherein the end cap comprises at least one internal fluid passageway at least in part defined by the at least one wall, the first interior surface, and the second interior surface, wherein the end cap comprises a gap between the at least one internal fluid passageway and an exterior of the end cap, wherein the gap is in a position inferior to the at least one aperture, wherein the at least one internal fluid passageway is in fluid communication with the at least one aperture to divert liquid to an exterior of the housing through the gap.

2. A liquid diversion assembly according to claim 1, wherein the proximal panel comprises at least one recess in the first interior surface, wherein the at least one recess is substantially aligned with the at least one aperture.

3. A liquid diversion assembly according to claim 2, wherein the at least one wall extends along the first interior surface and the second interior surface to substantially surround the at least one recess, wherein the at least one wall comprises the gap in a position inferior to the at least one recess, configured to permit flow of liquid from the internal fluid passageway to the exterior of the end cap.

4. A liquid diversion assembly according to claim 2, wherein an inferior surface of the at least one recess is angled from a superior position to an inferior position at the first interior surface.

5. A liquid diversion assembly according to claim 2, wherein the proximal panel comprises a guide protrusion surrounding each one of the at least one recesses, wherein the guide protrusion projects from the first interior surface towards the second interior surface, wherein an air gap is retained between the guide protrusion and the second interior surface.

6. A liquid diversion assembly according to claim 5, wherein the guide protrusion comprises a radially outward facing surface and a radially inward facing surface meeting at an apex.

7. A liquid diversion assembly according to claim 5, wherein each guide protrusion comprises a raised base surrounding the recess, and a guide projection extending from the raised base.

8. A liquid diversion assembly according to claim 7, wherein a plateau portion is provided between a radially outward edge of the raised base and the guide projection.

9. A liquid diversion assembly according to claim 1, wherein the at least one wall comprises a first wall extending from the first interior surface, and a second wall extending from the second interior surface, wherein the proximal panel and the distal panel are configured such that when connected the first wall and the second wall cooperate to form the internal fluid passageway.

10. A liquid diversion assembly according to claim 1, wherein the panels are joined to form a unitary part.

11. A liquid diversion assembly according to claim 1, wherein the panels are mechanically, thermally or ultrasonically bonded.

12. A liquid diversion assembly according to claim 1, wherein the compatible accessory is a humidifier.

13. A liquid diversion assembly according to claim 1, wherein the medical device is a ventilator.

14. An apparatus for supplying a flow of breathable gas at a positive pressure for respiratory therapy, wherein the apparatus comprises:

a liquid diversion assembly as claimed in claim 1, a pressure generator inside the housing for generating the flow of breathable gas and supplying the flow to an outlet;

wherein the end cap of the liquid diversion assembly is configured to be secured relative to the housing containing at least the pressure generator.

15. A respiratory treatment system, comprising:

an apparatus for supplying a flow of breathable gas at a positive pressure for respiratory therapy as claimed in claim 14;

a humidifier apparatus to change the absolute humidity of a flow of air for delivery to an entrance of the airways of a patient, the change being compared to the absolute humidity of ambient air, wherein the humidifier apparatus is configured to be selectively coupled to the apparatus for supplying a flow of breathable gas via the at least one aperture of the end cap.

16. A liquid diversion assembly for a medical device that includes a housing, the liquid diversion assembly comprising:

an end cap in association with the housing, the end cap comprising:

a proximal panel proximal to the medical device in use, comprising a first interior surface and a first exterior surface;

a distal panel distal to the medical device in use, comprising a second interior surface and a second exterior surface;

at least one wall extending between the first interior surface and the second interior surface;

at least one aperture for selective coupling with a compatible accessory, wherein the at least one aperture is between the second exterior surface and the second interior surface of the distal panel, wherein the end cap comprises at least one internal fluid passageway in fluid communication with the at least one aperture to divert liquid to an exterior of the housing, wherein the internal fluid passageway is at least in part defined by the at least one wall, the first interior surface, and the second interior surface, wherein the medical device is a ventilator.

17. An apparatus for supplying a flow of breathable gas at a positive pressure for respiratory therapy, wherein the apparatus comprises:

a pressure generator for generating the flow of breathable gas and supplying the flow to an outlet;

a housing which contains at least the pressure generator;

a liquid diversion assembly comprising:

an end cap in association with the housing, the end cap comprising:

a proximal panel proximal to the medical device in use, comprising a first interior surface and a first exterior surface;

a distal panel distal to the medical device in use, comprising a second interior surface and a second exterior surface;

at least one wall extending between the first interior surface and the second interior surface;

at least one aperture for selective coupling with a compatible accessory, wherein the at least one aperture is between the second exterior surface and the second interior surface of the distal panel, wherein the end cap comprises at least one internal fluid passageway in fluid communication with the at least one aperture to divert liquid to an exterior of the housing, wherein the internal fluid passageway is at least in part defined by the at least one wall, the first interior surface, and the second interior surface, wherein the end cap of the liquid diversion assembly is configured to be secured relative to the housing containing at least the pressure generator.

18. A respiratory treatment system, comprising:

an apparatus for supplying a flow of breathable gas at a positive pressure for respiratory therapy as claimed in claim 17;

a humidifier apparatus to change the absolute humidity of a flow of air for delivery to an entrance of the airways of a patient, the change being compared to the absolute humidity of ambient air, wherein the humidifier apparatus is configured to be selectively coupled to the apparatus for supplying a flow of breathable gas via the at least one aperture of the end cap.

* * * * *